(12) United States Patent
Coward et al.

(10) Patent No.: US 10,227,406 B2
(45) Date of Patent: Mar. 12, 2019

(54) CANNABINOID RECEPTOR-1 (CB1) MONOCLONAL ANTIBODIES

(71) Applicant: AMGEN INC., Thousand Oaks, CA (US)

(72) Inventors: Peter Coward, San Francisco, CA (US); Steven A. Moore, Jr., Poway, CA (US); Shi-Yuan Meng, Simi Valley, CA (US); Mei-Mei Tsai, Thousand Oaks, CA (US); Chadwick Terence King, North Vancouver (CA); Aaron Avraham Nazarian, Los Angeles, CA (US)

(73) Assignee: AMGEN, INC, Thousand Oaks, CA (US)

( * ) Notice: Subject to any disclaimer, the term of this patent is extended or adjusted under 35 U.S.C. 154(b) by 0 days.

(21) Appl. No.: 14/899,551

(22) PCT Filed: Jun. 25, 2014

(86) PCT No.: PCT/US2014/044164
§ 371 (c)(1),
(2) Date: Dec. 17, 2015

(87) PCT Pub. No.: WO2014/210205
PCT Pub. Date: Dec. 31, 2014

(65) Prior Publication Data
US 2016/0145333 A1    May 26, 2016

Related U.S. Application Data

(60) Provisional application No. 61/839,458, filed on Jun. 26, 2013.

(51) Int. Cl.
*C07K 16/28* (2006.01)

(52) U.S. Cl.
CPC .......... *C07K 16/28* (2013.01); *C07K 2317/21* (2013.01); *C07K 2317/24* (2013.01); *C07K 2317/31* (2013.01); *C07K 2317/34* (2013.01); *C07K 2317/565* (2013.01); *C07K 2317/76* (2013.01); *C07K 2317/92* (2013.01)

(58) Field of Classification Search
CPC ................ C07K 16/28; C07K 2317/21; C07K 2317/92; C07K 2317/24; C07K 2317/31; C07K 2317/565; C07K 2317/34; C07K 2317/76
See application file for complete search history.

(56) References Cited

U.S. PATENT DOCUMENTS

2013/0059890 A1    3/2013    Van Der Poorten et al.

FOREIGN PATENT DOCUMENTS

| WO | 2005/023232 A2 | 3/2005 |
|---|---|---|
| WO | 2009/059264 | 5/2009 |
| WO | 2009/087351 | 7/2009 |
| WO | 2010/075269 | 7/2010 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Di Marzo et al. (2008), "CB1 receptor antagonism biological basis for metabolic effects", Drug Disc. Today, 13(23-24):1026-1041.
Kuang et al. (2012), "A novel monoclonal antibody against cannabinoid receptor 1", Hybridoma, 31(2):131-136.
Sanz et al. (2004), "Antibodies and gene therapy: teaching old 'magic bullets' new tricks", Trends in Immunol., 25(2):85-91.
Tam et al. (2010), "Peripheral CB1 cannabinoid receptor blockade improves cardiometabolic risk in mouse models of obesity", J. Clin. Investigation, 120(8):2953-2966.
Tam et al. (2012), "Peripheral cannabinoid-1 receptor inverse agonism reduces obesity by reversing leptin resistance", Cell Metabol., 16:167-179.
Bernhardt, European Patent Office, International Search Report & Written Opinion for international application No. PCT/US2014/044164, dated Oct. 6, 2014.
Hutchings, et al., (2010), "Therapeutic antibodies directed at G protein-coupled receptors", mAbs, 2:594-606.
Klarenbeek, et al., (2012), "Targeting chemokines and chemokine receptors with antibodies", Drug Discover Today: Technologies; 9:e237-e244.
Leu, et al., (2010), "GPCT Somatostatin Receptor Extracellular Loop 2 is a Key Ectodomain for Making Subtype-Selective Antibodies With Agonist-Like Activities in the Pancreatic Neuroendocrine Tumor BON Cell Line", Pancreas, 39:1155-1166.
Peng, et al., (2016), "Molecular basis for the antagonistic activity of an anti-CXCR4 antibody", mAbs, 8:163-175.
Webb, et al., (2013), "Opportunities for Functional Selectivity in GPCR Antibodies", Biochem Pharmacol., 85:147-152.
Woolley, et al., (2013), "The role of ECL2 in CGRP receptor activation a combined modelling and experimental approach", JR Soc Interface 10:1-11.

* cited by examiner

*Primary Examiner* — Robert S Landsman
(74) *Attorney, Agent, or Firm* — Chenghua Luo

(57) ABSTRACT

This disclosure relates to CB1 receptor antigen-binding proteins, e.g. antibodies and methods of using the CB1 receptor antibodies. The CB1 receptor antibodies may comprise an antagonistic antibody to CB1 receptors and may be used to treat various health conditions. The health conditions can comprise obesity or diabetes or any disease that benefits from antagonism of the CB1 receptor.

17 Claims, 10 Drawing Sheets
Specification includes a Sequence Listing.

FIG. 2A

Heavy Chain Sequence

| | FR1 | CDR1 | FR2 | CDR2 | FR3 | CDR3 |
|---|---|---|---|---|---|---|
| 1A11 | QVQLQESGPGLVKPSQTLSLTCTVSGGSIR | RGGDYWS | WIRQHPGKGLEWIGY | IYYSGSTYYNPSLKS | RVTISVDTSKNQFSLKLSSVTAADTAVYYCAR | DYDILTGYYNSYYYGMDV |
| 1E9 | ------------------------------ | ------- | --------------- | -------T------- | -------------------------------- | ------------------ |
| 10D10 | ------------------------------ | ------- | --------------- | ------N-------- | -------------A---------------- | ------------------ |
| 46A1 | ------------S----------------- | ------- | --------------- | ------N------R- | -------------------------------- | ------------------ |
| 46G3 | ------------S----------------- | ------- | --------------- | ------N------R- | -------------------------------- | ------------------ |
| 48E2 | ------------S----------------- | ------- | --------------- | ------N------R- | -------------------------------- | ------------------ |
| 47F8 | ------------S----------------- | ------- | ----------Q---- | ------N------R- | -------------------------------- | ------------------ |
| 48D10 | ------------S---------------- | ------- | --------------- | -----IN------R- | -------------------------------- | ------------------ |
| 47C9 | ------------S----------------- | ------- | --------------- | H---T-N------R- | -------------I------------------ | ------------------ |
| 52B1 | ------------S----------------- | ------- | --------------- | ------S-------- | -------------------------------- | -----------F------ |
| 46Q5 | ------------S----------------- | ------- | --------------- | ------N------R- | -------------------------------- | ----------H------- |
| 46F6 | -----------Q------------------ | ------- | --------H------ | ------H-------- | ------------------------F--R---- | ----------T-----V- |
| 49H2 | -----------Q------------------ | ------- | --------H------ | ------H-------- | ------------------------F--R---- | ----------T-----V- |
| 46D10 | ------------S---------------- | ------- | --------------- | ------N------R- | -------------S------------------ | ----------V-----V- |
| 48C3 | ------------S----------------- | ------- | --------------- | ------N------R- | -------------------------------- | ----------V------- |
| 48H5 | ------------S----------------- | ------- | --------------- | ------N------R- | -------------------------------- | ---------E-------- |
| 52A1 | ------------S----------------- | ---N--- | --------------- | ------S-------- | -------------------------------- | ---------G-----F-- |
| 47B6 | ------------S----------------- | ------- | --------H------ | ------N-------- | ------------------------F--R---- | ---------H-T-----V- |

FIG. 2B

Light Chain Sequence

| | FR1 | CDR1 | FR2 | CDR2 | FR3 | CDR3 |
|---|---|---|---|---|---|---|
| | DIVMTQSPLSLPVTPGEPASISC | RSSQSLLHSNGYNYLD | WYLQKPGQSPQLLIY | LGSNRAS | GVPDRFSGSGSGTDFTLKISRVEAEDVGVYYC | MQALQTPRT |
| 1A11 | --------------------- | ---------------- | --------------- | ------- | -------------------------------- | --------- |
| 1E9 | --------------------- | ---------------- | --------------- | ------- | -----------------R-------------- | --------- |
| 10D10 | --------------------- | -------F-------- | --------------- | ------- | ----R--------------------------E- | --------- |
| 46A1 | --------------------- | -------T-------- | --------------- | ------- | --------------------------------E- | --------- |
| 46G3 | --------------------- | -------H-------- | --------------- | ------- | --------------------------------E- | --------- |
| 48E2 | --------------------- | -------F-------- | --------------- | ------- | --------------------------------E- | --------- |
| 47F8 | --------------------- | -------T-------- | --------------- | ------- | --------------------------------E- | --------- |
| 48D10 | --------------------- | -------D-------- | --------------- | ------- | -------------------------------VF- | --------- |
| 47C9 | --------------------- | ---------------- | --------------- | ------- | --------------------------------E- | --------- |
| 52B1 | --------------------- | --Y------------- | --------------- | ------- | ---------------T---------------- | --------- |
| 46D5 | --------------------- | -------F-------- | --------------- | ------- | ---------------------------------- | --------- |
| 46F6 | --------------------- | --S------------- | --------------- | --V---- | ---------------------------------- | --------- |
| 49H2 | --------------------- | --S------------- | --------------- | --V---- | --------------------------------E- | --------- |
| 46D10 | --------------------- | ---------------- | --------------- | ------- | --------------------------------F- | --------- |
| 48C3 | --------------------- | -------F-------- | --------------- | ------- | --------------------------------F- | --------- |
| 48H5 | --------------------- | --Y------------- | --------------- | ------- | ---------------------------F---- | --------- |
| 52A1 | --------------------- | ---------------- | --------------- | ------- | ---------------------------------- | --------- |
| 47B6 | --------------------- | --S------------- | --------------- | --V---- | ----------------------------G----- | --------- |

FIG. 3

| Antibody | cAMP EC50, nM | Thermal Stability, °C | Agitation Stability | Mutation Location |
|---|---|---|---|---|
| D83R | 57 | 67 | OK | HC FW |
| 41Y | 51 | 77 | OK | L-CDR2/H-CDR2 |
| 31Y | 69 | 77 | OK | L-CDR1/H-CDR2 |
| 8Y | 61 | 75 | OK | L-CDR1 |
| D83K/N35Y | 33 | 71 | OK | L-CDR1/HC FW |
| N35W | 60 | 77 | ND | L-CDR1 |
| 10D10 | 220 | 77 | OK | WT |

FIG. 4B

| | Un | IgG-PE | V5 | E3K | 3A4 | 3H7 | 10B4 | 10D2 | 10D10 | 1A11 | 1E9 | 5G4 |
|---|---|---|---|---|---|---|---|---|---|---|---|---|
| Mock | 1.9 | 3.6 | 2.2 | 12.7 | 4.0 | 3.7 | 4.3 | 4.3 | 3.4 | 3.8 | 3.5 | 3.3 |
| V5-mCB1 | 2.2 | 2.3 | 115.2 | 16.5 | 69.9 | 4.1 | 2.5 | 2.5 | 2.9 | 3.7 | 2.6 | 2.8 |
| V5-hCB1 | 2.2 | 2.3 | 100.9 | 15.9 | 79.8 | 124.6 | 2.6 | 3.0 | 125.7 | 124.8 | 121.3 | 117.5 |
| E3K-hCB1 del.NT | 2.0 | 2.1 | 2.7 | 19.9 | 2.8 | 45.9 | 2.4 | 2.4 | 49.6 | 48.1 | 46.9 | 38.5 |
| V5-hCB2/hCB1 ECL1-3 | 2.7 | 2.9 | 664.9 | 18.6 | 3.8 | 94.7 | 3.3 | 3.2 | 105.6 | 102.5 | 137.9 | 105.9 |
| V5-hCB1 R186P | 2.1 | 2.2 | 82.3 | 13.2 | 73.0 | 43.5 | 2.4 | 2.4 | 51.8 | 44.1 | 56.3 | 46.6 |
| V5-hCB1 E258K | 2.1 | 2.1 | 123.4 | 11.4 | 104.9 | 3.5 | 2.3 | 2.3 | 2.6 | 3.3 | 2.4 | 2.5 |
| V5-hCB1 H270L | 1.9 | 2.0 | 143.6 | 10.2 | 124.2 | 3.5 | 2.1 | 2.0 | 3.1 | 3.3 | 2.7 | 2.5 |

CANNABINOID RECEPTOR-1 (CB1) MONOCLONAL ANTIBODIES

CROSS-REFERENCE TO RELATED APPLICATIONS

This application claims the benefit of U.S. Provisional Application No. 61/839,458, filed Jun. 26, 2013, which is hereby incorporated by reference.

REFERENCE TO THE SEQUENCE LISTING

The present application is being filed along with a Sequence Listing in electronic format. The Sequence Listing is provided as a file entitled A-1835-WO-PCT_SEQ.txt created Jun. 25, 2014, which is 99,680 bytes in size. The information in the electronic format of the Sequence Listing is incorporated herein by reference in its entirety.

FIELD OF THE INVENTION

This disclosure relates to CB1 receptor antigen-binding proteins, e.g. antibodies and methods of using the CB1 receptor antibodies. The CB1 receptor antibodies may comprise antibodies that antagonize signaling of the cannabinoid receptor CB1.

BACKGROUND OF THE INVENTION

The CB1 receptor (cannabinoid receptor-1, gene name Cnr 1) is a Gi-coupled G-Protein Receptor that is widely expressed in the CNS and peripheral nervous system. Agonist stimulation of CB1 receptors leads to inhibition of adenyl cyclase activity and activation of mitogen-activated protein (MAP) kinase. CB1 receptors are highly conserved between human, mouse and rat.

CB1 receptors are among the most abundant and widely distributed G protein-coupled receptors in the mammalian brain. They are also found in peripheral tissues including adipose, liver, muscle and the gastrointestinal tract.

Endogenous agonists of the CB1 receptor can comprise anandamide and 2-arachidonoyl glycerol. Exogenous agonists can comprise $\Delta^9$-tetrahydrocannabinol. Small molecule antagonists or inverse agonists (used interchangeably) such as rimonabant or taranabant have been shown to reduce body weight and improve metabolic parameters, e.g. reduced plasma glucose and insulin levels.

Unfortunately, such small molecule antagonists have also been shown to have adverse CNS effects. For example, it has been reported that rimonabant, a CB1 small molecule receptor antagonist/inverse agonist which binds to CB1 receptors increased the incidence of anxiety, depression, and suicidal ideation in multiple clinical trials (NDA 21-888 FDA Briefing Document, Jun. 13, 2007)

Small molecule antagonists with poor brain penetration (for example AM6545 and JD5037) have been reported to reduce food intake and body weight gain and improve multiple metabolic parameters in mice (Tam et al, J. Clin. Invest. 120:2953-66, 2010; Tam et al Cell Metab 16:1-13, 2012). Additional peripherally-restricted small molecules have been described (US2011/0144157)

It is possible that the positive metabolic effects of CB1 antagonists can be mediated by peripheral receptors. Therefore, a peripherally-acting large molecule may be efficacious and safer than failed small molecule therapies.

SUMMARY OF THE INVENTION

The CB1 antagonistic antibodies disclosed herein are believed to be the only large molecule antagonists identified to date. While small molecule antagonists have been described by various groups, CB1 antagonistic antibodies may be distinguished from small molecule antagonists by e.g. lack of CNS penetration and different pharmacokinetic properties including reduced clearance resulting in less frequent administration.

The invention relates to CB1 receptor antigen-binding proteins and fragments thereof. The CB1 receptor antigen-binding proteins and fragments thereof that bind to CB1 receptors can be antagonistic CB1 receptor antigen-binding proteins. In various embodiments the antigen-binding proteins are antibodies. Uses are also provided for the antigen-binding proteins described herein.

Various embodiments of the invention are provided in this disclosure.

Embodiment 1 is an antigen-binding protein consisting essentially of SEQ ID NO: 4 and SEQ ID NO: 5 that specifically binds to SEQ ID NO: 1. Additional related embodiments may either consist of or comprise the amino acid sequences of the antigen-binding proteins.

Embodiment 2 is the antigen-binding protein of Embodiment 1, wherein the binding to SEQ ID NO: 1 antagonizes G-protein signaling as measured in a GTP-Eu assay, an Aequorin assay or cAMP assay.

Embodiment 3 is the antigen-binding protein of Embodiment 1, wherein said antigen-binding protein is a monoclonal antibody or fragment thereof.

Embodiment 4 is the antigen-binding protein of Embodiment 1, wherein said antigen-binding protein is a mouse antibody, a humanized antibody, a human antibody, a chimeric antibody or a multispecific antibody.

Embodiment 5 is the antigen-binding protein of Embodiment 1, wherein the antigen-binding protein binds to the extracellular loop 2 (EC2) domain region of the human CB1 receptor as indicated in FIG. 1. The exact EC2 domain may be represented in various embodiments by a fewer or greater number of amino acids.

Embodiment 6 is the antigen-binding protein of Embodiment 5, wherein the antigen-binding protein binds specifically to the amino acids NCEKLQSVCSDIFPHIDE (residues 256-273) of SEQ ID NO: 1.

Embodiment 7 is the antigen-binding protein of Embodiment 6, wherein the antigen-binding protein binds to at least 15 of the amino acids of the amino acid sequence NCEKLQSVCSDIFPHIDE.

Embodiment 8 is the antigen-binding protein of Embodiment 7, wherein the antigen-binding protein binds to at least 10 of the amino acids of the amino acid sequence NCEKLQSVCSDIFPHIDE.

Embodiment 9 is the antigen-binding protein of Embodiment 1, wherein the antigen-binding protein has an $EC_{50}$ less than 250 nM in a cAMP assay.

Embodiment 10 is the antigen-binding protein of Embodiment 9, wherein the antigen-binding protein has an $EC_{50}$ less than 100 nM in a cAMP assay. In various embodiments the antigen-binding proteins may have an $EC_{50}$ in the picomolar range.

Embodiment 11 is an antigen-binding protein having at least 99% identity to SEQ ID NO: 4 and SEQ ID NO: 5.

Embodiment 12 is an antigen-binding protein comprising SEQ ID NOs: 17-22, SEQ ID NOs. 36-37 or SEQ ID Nos. 36 and 38 that specifically binds to SEQ ID NO:1. Additional related embodiments may either consist of or consist essentially of the amino acid sequences of the antigen-binding sequences.

Embodiment 13 is the antigen-binding protein of Embodiment 12, wherein the binding to SEQ ID NO: 1 antagonizes G-protein signaling as measured in a GTP-Eu assay, an Aequorin assay or cAMP assay.

Embodiment 14 is the antigen-binding protein of Embodiment 12, wherein said antigen-binding protein is a monoclonal antibody or fragment thereof.

Embodiment 15 is the antigen-binding protein of Embodiment 14, wherein said antigen-binding protein is a mouse antibody, a humanized antibody, a human antibody, a chimeric antibody, a multispecific antibody.

Embodiment 16 is the antigen-binding protein of Embodiment 12, where the antigen-binding protein binds to the EC2 domain region of the human CB1 receptor as indicated in FIG. 1. The exact EC2 domain may be represented by a fewer or greater number of amino acids.

Embodiment 17 is the antigen-binding protein of Embodiment 16, wherein the antigen-binding protein binds specifically to the amino acids NCEKLQSVCSDIFPHIDE (residues 256-273) of SEQ ID NO: 1.

Embodiment 18 is the antigen-binding protein of Embodiment 17, wherein the antigen-binding protein binds to at least 15 of the amino acids of the amino acid sequence NCEKLQSVCSDIFPHIDE.

Embodiment 19 is the antigen-binding protein of Embodiment 18, wherein the antigen-binding protein binds to at least 10 of the amino acids of the amino acid sequence NCEKLQSVCSDIFPHIDE.

Embodiment 20 is the antigen-binding protein of Embodiment 12, wherein the antigen-binding protein has an $EC_{50}$ of less than 300 nM in a cAMP assay.

Embodiment 21 is the antigen-binding protein of Embodiment 20, wherein the antigen-binding protein has an $EC_{50}$ of less than 100 nM in a cAMP assay. In various embodiments the antigen-binding proteins may have an $EC_{50}$ in the picomolar range.

Embodiment 22 is an antigen-binding protein having at least 99% identity to SEQ ID NOs: 17-22.

Embodiment 22 is an antigen-binding protein comprising SEQ ID Nos 7 and 8, SEQ ID NOs: 7 and 10, SEQ ID NOs: 7 and 12, SEQ ID NOs: 6 and 16, SEQ ID NOs: 4 and 14, SEQ ID Nos. 36 and 37 or SEQ ID Nos. 36 and 38 that specifically binds to SEQ ID NO: 1. Additional related embodiments may either consist of or consist essentially of the amino acid sequences of the antigen-binding sequences.

Embodiment 23 is the antigen-binding protein of Embodiment 22, wherein the binding to SEQ ID NO: 1 antagonizes G-protein signaling as measured in a GTP-Eu assay, an Aequorin assay or cAMP assay.

Embodiment 24 is the antigen-binding protein of Embodiment 22, wherein said antigen-binding protein is a monoclonal antibody or fragment thereof.

Embodiment 25 is the antigen-binding protein of claim 24, wherein said antigen-binding protein is a mouse antibody, a humanized antibody, a human antibody, a chimeric antibody, a multispecific antibody.

Embodiment 26 is the antigen-binding protein of Embodiment 22, where the antigen-binding protein binds to the EC2 domain region of the human CB1 receptor as illustrated in FIG. 4A. The exact EC2 domain may be represented by a fewer or greater number of amino acids.

Embodiment 27 is the antigen-binding protein of Embodiment 26, wherein the antigen-binding protein binds to the amino acids NCEKLQSVCSDIFPHIDE (residues 256-273) of SEQ ID NO: 1.

Embodiment 28 is the antigen-binding protein of Embodiment 27, wherein the antigen-binding protein binds to at least 15 of the amino acids of the amino acid sequence NCEKLQSVCSDIFPHIDE.

Embodiment 29 is the antigen-binding protein of Embodiment 28, wherein the antigen-binding protein binds to at least 10 of the amino acids of the amino acid sequence NCEKLQSVCSDIFPHIDE.

Embodiment 30 is the antigen-binding protein of Embodiment 22, wherein the antigen-binding protein has an $EC_{50}$ less than 300 nM in a cAMP assay Embodiment 31 is the antigen-binding protein of Embodiment 30, wherein the antigen-binding protein has an $EC_{50}$ less than 100 nM in a cAMP assay. In various embodiments the antigen-binding proteins may have an $EC_{50}$ in the picomolar range.

Embodiment 32 is an antigen-binding protein having at least 99% identity to one of the antigen binding proteins of Embodiment 22.

Embodiment 33 is a nucleic acid encoding the antigen-binding protein of any one of Embodiments 1, 12 or 22.

Embodiment 34 is an expression vector comprising the nucleic acid of Embodiment 33.

Embodiment 35 is a host cell comprising the vector of Embodiment 34.

Embodiment 36 is the host cell of Embodiment 35 wherein the cell is a eukaryotic or prokaryotic cell.

Embodiment 37 is the host cell of Embodiment 36 wherein the eukaryotic cell is a mammalian cell.

Embodiment 38 is a method of producing an antigen-binding protein, comprising culturing the host cell of Embodiment 37 under suitable conditions such that the nucleic acid is expressed to produce the antigen binding protein.

Embodiment 39 is the method of Embodiment 38, further comprising recovering the antibody from a culture of the host cell.

Embodiment 40 is a composition comprising the antigen-binding protein of any one of Embodiments 1, 12, 22 or 44 and a pharmaceutically acceptable carrier, diluent or excipient.

Embodiment 41 is a method for treating a patient in need of antagonizing the CB1 receptor comprising administering the composition of Embodiment 40.

Embodiment 42 is the method of Embodiment 32 wherein the treating of a patient results in reduced body weight or improved metabolic parameters.

Embodiment 43 is the method of Embodiment 42, wherein the improved metabolic parameters are reduced plasma glucose, reduced insulin levels, reduced triglyceride levels, reduced HbA1c, reduced intraabdominal, liver fat, reduced blood pressure, increased adiponectin, increased HDL cholesterol or increased energy expenditure.

Embodiment 44 is an antigen-binding protein that specifically binds to SEQ ID NO: 1 and antagonizes G-protein signaling as measured in a GTP-Eu assay, an Aequorin assay or cAMP assay.

Embodiment 45 is an antigen-binding protein of Embodiment 44, wherein said antigen-binding protein is a monoclonal antibody or fragment thereof.

Embodiment 46 is the antigen-binding protein of Embodiment 45, wherein said antigen-binding protein is a mouse antibody, a humanized antibody, a human antibody, a chimeric antibody or a multispecific antibody.

Embodiment 47 is the antigen-binding protein of Embodiment 44, wherein the antigen-binding protein binds to the EC2 domain region of the human CB1 receptor. The exact EC2 domain may be represented by a fewer or greater number of amino acids Embodiment 48 is the antigen-binding protein of Embodiment 47, wherein the antigen-binding protein binds specifically to the amino acids NCEKLQSVCSDIFPHIDE (residues 256-273) of SEQ ID NO: 1.

Embodiment 49 is the antigen-binding protein of claim 48, wherein the antigen-binding protein binds to at least 15 of the amino acids of the amino acid sequence NCEKLQSVCSDIFPHIDE.

Embodiment 50 is the antigen-binding protein of claim 48, wherein the antigen-binding protein binds to at least 10 of the amino acids of the amino acid sequence NCEKLQSVCSDIFPHIDE.

Embodiment 51 is the antigen-binding protein of Embodiment 44, wherein the antigen-binding protein has an $EC_{50}$ less than 250 nM in a cAMP assay.

Embodiment 52 is the antigen-binding protein of Embodiment 51, wherein the antigen-binding protein has an $EC_{50}$ of less than at least 100 nM in a cAMP assay. In various embodiments the antigen-binding proteins may have an $EC_{50}$ in the picomolar range.

Other embodiments will be appreciated by one skilled in the art, and are described herein. Although various embodiments have been described above, those skilled in the art will readily appreciate that the examples and studies detailed herein are only illustrative. It should be understood that various modifications can be made without departing from the spirit of the invention.

BRIEF DESCRIPTION OF THE DRAWINGS

FIGS. 2A and 2B provide a comparison of the heavy chain and light chain protein sequences of various anti-CB1 antibodies. It shows amino differences in the framework and CDR regions of the HC and LC protein sequences between several clones.

FIG. 3 presents additional characterization of wild-type and mutant versions of CB1 antagonist antibody 10D10.

FIGS. 4A-4C shows mutations made to the CB1 receptor that assist in providing antibody binding sites. FIG. 4A is a cartoon describing the mutants, FIG. 4B shows FACS binding data, and FIG. 4C shows aequorin signaling data.

DETAILED DESCRIPTION

Figure 1:
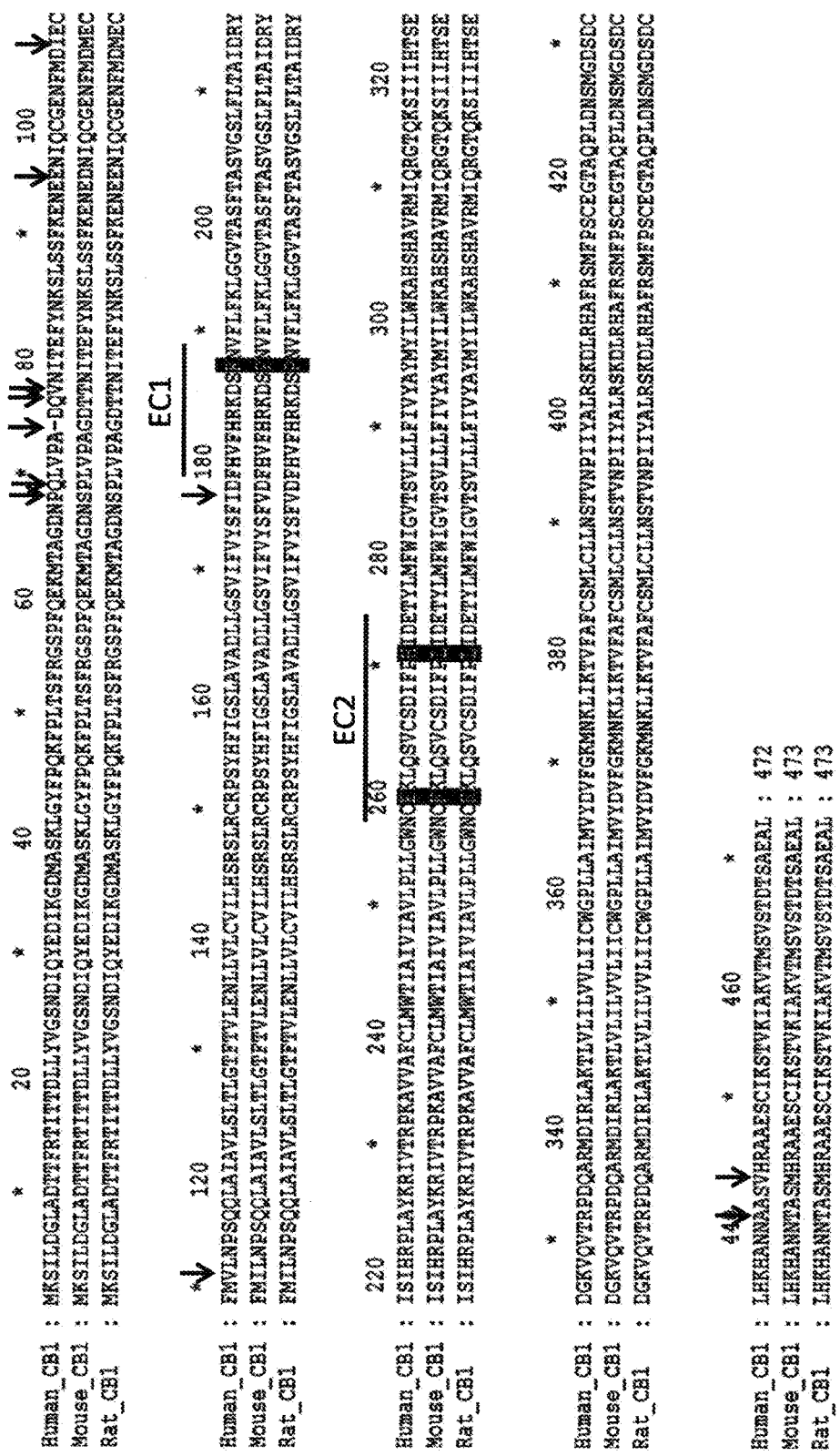
FIG. 1 shows the alignment of human (SEQ ID NO: 1), mouse (SEQ ID NO: 2), and rat (SEQ ID NO: 3) CB1 protein sequences, with the approximate locations of extracellular loops 1 and 2 (EC1 and EC2—also referred to as the EC domain regions) indicated by a solid line above the sequences. Residues used in the epitope mapping studies shown in FIG. 4 are indicated in FIG. 1 by black shading-EC1 (R186P-between human sequence and mouse/rat sequence) and positions (E258K-between human sequence and mouse/rat sequence) and (H270L-between human sequence and mouse/rat sequence) in EC2. It should be noted that the position numbers above the sequences are provided for convenience and do not necessarily align exactly. Additional differences between the human and rodent sequences are indicated by arrows.

CB1 receptor antigen-binding proteins (such as antibodies and functional binding fragments thereof) that bind to CB1 receptors are disclosed herein. The antigen-binding proteins bind to CB1 receptors and prevent the CB1 receptors from functioning in various ways, e.g. antagonize receptor activity. CB1 receptor binding proteins may bind to the CB1 receptors and prevent signaling as measured, for example, in cAMP assays, Aequorin assays or GTP-Eu assays.

The foregoing summary is not intended to define every aspect or embodiment of the invention, and additional aspects may be described in other sections. The entire document is intended to be related as a unified disclosure, and it should be understood that all combinations of features described herein may be contemplated, even if the combination of features is not found together in the same sentence, paragraph, or section of this document.

In addition to the foregoing, as an additional aspect, all embodiments narrower in scope in any way than the variations defined by specific paragraphs herein can be included in this disclosure. For example, certain aspects may be described as a genus, and it should be understood that every member of a genus can be, individually, an embodiment. Also, aspects described as a genus or selecting a member of a genus should be understood to embrace combinations of two or more members of the genus. It should also be understood that while various embodiments in the specification may be presented using "comprising" language, under various circumstances, a related embodiment may also be described using "consisting of" or "consisting essentially of" language.

It will be understood that the descriptions herein are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

It should also be understood that when describing a range of values, the characteristic being described could be an individual value found within the range. For example, "a pH from about pH 4 to about pH 6," could be, but is not limited to, pH 4, 4.2, 4.6, 5.1, 5.5, etc. and any value in between such values. Additionally, "a pH from about pH 4 to about pH 6," should not be construed to mean that the pH in question varies 2 pH units from pH 4 to pH 6, but rather a value may be picked from within a two pH range for the pH of the solution.

In some embodiments, when the term "about" is used, it means the recited number plus or minus 5%, 10%, 15% or more of that recited number. The actual variation intended is determinable from the context.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the disclosure, the following terms, unless otherwise indicated, shall be understood to have the following meanings:

As used herein the term "CB1" refers to the cannabinoid receptor-1 which is a Gi-coupled G-Protein Receptor that is widely expressed in the CNS and peripheral nervous system.

Stimulation of CB1 receptors is known to inhibit adenyly cyclase and activate mitogen-activated protein (MAP) kinase. The CB1 protein sequence is highly conserved between human, mouse and rat. CB1 receptors are among the most abundant and widely distributed G protein-coupled receptors in the mammalian brain. They are also found in other tissues including adipose, liver, muscle and the gastrointestinal tract As used herein, an antibody or antigen-binding fragment can be an agonist or an antagonist.

An "agonist" refers to an agent that binds to a polypeptide (such as a receptor), or a polynucleotide and inter alia stimulates, increases, activates, facilitates, enhances activation, sensitizes or up regulates the activity or expression of the polypeptide or polynucleotide.

An "antagonist" refers to an agent that binds to a polypeptide (such as a receptor) or a polynucleotide and inter alia partially or totally blocks stimulation, decreases, prevents, delays activation, inactivates, desensitizes, or down regulates the activity of the polypeptide or polynucleotide. An antagonist may also be an inverse agonist which among other things may decrease constitutive signaling of a receptor.

An "antigen binding protein" ("ABP") refers to any protein that binds a specified target antigen. In this specification, the specified target antigen can be a CB1 receptor or fragment or region thereof. "Antigen-binding protein" includes but is not limited to antibodies and binding parts thereof, such as immunologically functional fragments. Peptibodies are another example of antigen-binding proteins.

A "CB1 receptor antigen-binding protein" refers to a protein that can bind the CB1 receptor. The "CB1 receptor antigen-binding protein" can be a "CB1 receptor antagonistic antibody" that binds the receptor. The CB1 receptor antibody can block the signaling of the CB1 receptor. Blocking the signaling can have both a cellular and a physiological response, such as reducing body weight and improving metabolic parameters, e.g. reducing plasma glucose and insulin levels.

"Extracellular (EC) binding regions" of the CB1 protein are shown in FIG. 1 and can also be referred to as "extracellular loops" or "extracellular domain regions." For example, the EC2 domain region is believed to have the sequence NCEKLQSVCSDIFPHIDE (residues 256-273) of SEQ ID NO: 1. In various embodiments the EC2 domain region may further comprise 1, 2, 3, 4 or 5 additional amino acids at either the amino or carboxyl end of the sequence. In other embodiments, the EC2 domain region may have 1, 2, 3, 4 or 5 fewer amino acids at either the amino or carboxyl end of the sequence. The antibodies disclosed in this application may bind to any of the EC2 domains described above or to the sequence NCEKLQSVCSDIFPHIDE (residues 256-273) of SEQ ID NO: 1. or to at least 10 or at least 15 amino acids of that sequence. Various antibodies may alternatively bind to the EC1 domain region as shown in FIG. 1.

The term "polynucleotide" or "nucleic acid" includes both single-stranded and double-stranded nucleotide polymers. Nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are about 10 to about 60 bases in length. In other embodiments, oligonucleotides are about 12, about 13, about 14, about 15, about 16, about 17, about 18, about 19, or about 20 to about 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences. In various embodiments the nucleic acid described can be an "isolated nucleic molecules."

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

A nucleic acid can encode antigen-binding proteins disclosed in various embodiments herein, e.g. a CB1 receptor antigen-binding protein or anti-CB1 receptor antibody. The nucleic acid is said to be "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "amino acid" refers to natural and/or non-naturally occurring amino acids, and includes its normal meaning in the art. The amino acids may also be referred to as canonical or non-canonical amino acids.

The terms "polypeptide" or "protein" means a macromolecule having the amino acid sequence of a native protein, i.e., a protein produced by a naturally-occurring and non-recombinant cell; or the protein can be produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" encompass inter alia, CB1 receptor antigen-binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In various embodiments, fragments can be about five to about 500 amino acids long. For example, fragments can be at least about 5, about 6, about 8, about 10, about 14, about 20, about 50, about 70, about 100, about 150, about 200, about 250, about 300, about 350, about 400, or about 450 amino acids long. Useful polypeptide fragments include immunologically functional fragments of antibodies, including binding domains. In the case of an CB1 receptor-binding antibody, useful fragments include but are not limited to a CDR region, a variable domain of a heavy and/or light chain, a portion of an antibody chain or just its variable region including one, two, three, four, five or six CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or non-covalent interaction) with a polypeptide with which it is not associated in nature, or (6) does not occur in nature. An isolated protein can be a CB1 antigen binding protein or antibody. Typically, an "isolated protein" can constitute at least about 5%, at least about 10%, at least about 25%, at least about 50%, at least about 75%, at least about 90% or more of a given sample. Genomic DNA, cDNA, mRNA or other RNA, of synthetic origin, or any combination thereof can encode such an isolated protein. In various embodiments, the isolated protein is substantially free from proteins or polypeptides or other contaminants that are found in its natural environment that would interfere with its therapeutic, diagnostic, prophylactic, research or other use. An isolated "antigen-binding protein" or an "isolated antibody" can be considered an "isolated protein." In various embodiments the antigen-binding protein can be an isolated antigen-binding protein or an isolated antibody.

A "variant" or "mutant" of a polypeptide (e.g., an antigen-binding protein, or an antibody) comprises an amino acid sequence wherein one or more amino acid residues are inserted into, deleted from and/or substituted into the amino acid sequence relative to another polypeptide sequence. Variants include fusion proteins.

As used herein, the twenty conventional (canonical or naturally occurring) amino acids and their abbreviations follow conventional usage. See Immunology-A Synthesis (2nd Ed., E. S. Golub & D. R. Gren, Eds., Sinauer Assoc., Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides of various embodiments described herein. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:

Hydrophobic: Norleucine, Met, Ala, Val, Leu, Ile;
Neutral hydrophilic: Cys, Ser, Thr, Asn, Gln;
Acidic: Asp, Glu;
Basic: His, Lys, Arg;
Residues that influence chain orientation: Gly, Pro; and
Aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to an antigen-binding protein (such as an antibody), according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte, et al., J. Mol. Biol., 157:105-131, (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions."

Exemplary amino acid substitutions are set forth in Table 1.

TABLE 1

AMINO ACID SUBSTITUTIONS

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen-binding protein can have a greater circulating half-life than an antigen-binding protein that is not chemically modified. In certain embodiments, a chemically modified antigen-binding protein can have improved targeting capacity for desired cells, tissues, and/or organs. In some embodiments, a derivative antigen-binding protein is covalently modified to include one or more water soluble polymer attachments, including, but not limited to, polyethylene glycol, polyoxyethylene glycol, or polypropylene glycol. See e.g., U.S. Pat. Nos. 4,640,835; 4,496,689; 4,301,144; 4,670,417; 4,791,192 and 4,179,337. In certain embodiments, a derivative antigen-binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen-binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29, (1986); Veber & Freidinger, TINS, p. 392, (1985); and Evans et al., J. Med. Chem., 30:1229, (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by at least one linkage selected from: —CH$_2$NH—, —CH$_2$S—, —CH$_2$—CH$_2$—, —CH=CH-(cis & trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo & Gierasch, Ann. Rev. Biochem., 61:387, (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

The terms "identical" or percent "identity," in the context of two or more nucleic acids or polypeptide sequences, refer to two or more sequences or subsequences that are the same or have a specified percentage of amino acid residues or nucleotides that are the same (e.g. in various embodiments an antigen binding protein may have about 60% identity, about 65%, about 70%, about 75%, about 80%, about 85%, about about 90%, about 91%, about 92%, about 93%, about 94%, about 95%, about 96%, about 97%, about 98%, about 99%, or higher identity to sequences presented herein, over a specified region, when compared and aligned for maximum correspondence over a comparison window or designated region) as measured using a BLAST or BLAST 2.0 sequence comparison algorithms with default parameters described below, or through manual alignment and also visual inspection (see e.g., the NCBI website http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described herein, the algorithms can account for gaps, and the like. In various embodiments, identity exists over a region that is at least about 25 amino acids, about 50 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window" includes reference to a segment of any one of the number of contiguous positions as desired. In some embodiments the "comparison window" can be selected from the group consisting of from about 50 to about 200, or about 100 to about 150, or greater than 150, if so desired in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. AppL Math.*, 2:482, (1981), by the homology alignment algorithm of Needleman & Wunsch, *J. Mol. Biol.*, 48:443, (1970), by the search for similarity method of Pearson & Lipman, *Proc. Nat'l. Acad. Sci. USA*, 85:2444, (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see e.g., *Current Protocols in Molecular Biology* (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.*, 25:3389-3402, (1977) and Altschul et al., *J. Mol. Biol.*, 215:403-410, (1990), respectively. BLAST and BLAST 2.0 are used, with the parameters described herein, to determine percent sequence identity for the nucleic acids and proteins of various embodiments. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA*, 89:10915, (1989)) alignments (B) of 50, expectation (E) of 10, M=5, N=−4, and a comparison of both strands.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto. The expression vectors useful in various embodiments described herein can contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic makeup to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells. A transfection may be transient.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "immunologically functional fragment" (or simply "fragment") of an antibody or immunoglobulin chain (heavy or light chain) antigen-binding protein, as used herein, is a species of antigen-binding protein comprising a portion (regardless of how that portion is obtained or synthesized) of an antibody that lacks at least some of the amino acids present in a full-length chain but which is still capable of specifically binding to an antigen.

"Specific binding," "specifically binds" or "binds specifically" should be understood to mean that the antigen-binding protein preferentially binds CB1. This does not necessarily preclude, however, binding of an antigen-binding protein to proteins other than CB1. In various embodiments, the binding to other proteins represents less than about 5%, less than about 10%, less than about 15%, less than about 20% or less than about 25% of the total protein bound. A "specifically binding" CB1 antigen binding protein, predominantly binds CB1 or a specified sequence of CB1, e.g. to an extracellular domain of CB1. "Binds specifically" or "binds specifically" should not be construed to exclude binding to other than the target(s) or specific sequence recited, however the predominant binding activity should be for the specified target(s) or amino acid sequence.

Fragments of antigen-binding proteins are biologically active in that they bind to the target antigen and can compete with other antigen-binding proteins, including intact antibodies, for binding to a given epitope or antigen. In some embodiments, the fragments are neutralizing fragments. In some embodiments, the fragments can block or reduce the likelihood of the interaction between CB1 and its ligand(s). In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen-binding proteins, including intact antibodies Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')$_2$, Fv, domain antibodies and single-chain antibodies, and can be derived from any mammalian source, including but not limited to human, mouse, rat, camelid or rabbit. It is further contemplated that a functional portion of the antigen-binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen-binding protein can include nonprotein components.

Certain antigen-binding proteins described herein are antibodies or are derived from antibodies. In certain embodiments, the polypeptide structure of the antigen-binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen-binding protein comprises or consists of avimers (tightly binding peptide).

An "Fc" region comprises two heavy chain fragments comprising the $C_H1$ and $C_H2$ domains of an antibody. The two heavy chain fragments are held together by two or more disulfide bonds and by hydrophobic interactions of the $C_H3$ domains.

A "Fab fragment" comprises one light chain and the $C_H1$ and variable regions of one heavy chain. The heavy chain of a Fab molecule cannot form a disulfide bond with another heavy chain molecule.

A "Fab' fragment" comprises one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

A "bivalent antigen-binding protein" or "bivalent antibody" comprises two antigen-binding sites. In some instances, the two binding sites have the same antigen specificities. Bivalent antigen-binding proteins and antibodies can be bispecific as defined herein. A bivalent antibody other than a "multispecific" or "multifunctional"

antibody, in certain embodiments, typically is understood to have each of its binding sites identical.

A "multispecific antigen-binding protein" or "multispecific antibody" is one that targets more than one antigen or epitope.

A "bispecific," "CB1-specific," or "bifunctional" antigen-binding protein or antibody is a hybrid antigen-binding protein or antibody, respectively, having two different antigen-binding sites. Bispecific antigen-binding proteins and antibodies are a species of multispecific antigen-binding protein antibody and can be produced by a variety of methods including, but not limited to, fusion of hybridomas or linking of Fab' fragments. See e.g., Songsivilai and Lachmann, 1990, *Clin. Exp. Immunol.*, 79:315-321; Kostelny et al., 1992, *J. Immunol.*, 148:1547-1553. The two binding sites of a bispecific antigen-binding protein or antibody will bind to two different epitopes, which can reside on the same or different protein targets.

Each individual CB1 immunoglobulin chain is typically composed of several "immunoglobulin domains." These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as $C_H1$, $C_H2$ and $C_H3$. The antibodies that are provided can have any of these isotypes and subtypes "Antigen-binding region" means a protein, or a portion of a protein, that specifically binds a specified antigen (e.g., a paratope). For example, that portion of an antigen-binding protein that contains the amino acid residues that interact with an antigen and confer on the antigen-binding protein its specificity and affinity for the antigen is referred to as "antigen-binding region." An antigen-binding region typically includes one or more Complementary Binding Regions (CDRs). Certain antigen-binding regions also include one or more "framework" regions. A "CDR" is an amino acid sequence that contributes to antigen-binding specificity and affinity. "Framework" regions can aid in maintaining the proper conformation of the CDRs to promote binding between the antigen-binding region and an antigen. Structurally, framework regions can be located in antibodies between CDRs.

In certain aspects, recombinant antigen-binding proteins that bind CB1 receptors, are provided. In this context, a "recombinant antigen-binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen-binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen-binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" and one full-length "heavy" chain. The amino-terminal portion of each chain typically includes a variable region that typically is responsible for antigen recognition. The carboxy-terminal portion of each chain typically defines a constant region that can be responsible for effector function. The variable regions of each light/heavy chain pair typically form the antigen-binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md., (1987 and 1991), or Chothia & Lesk, *J. Mol. Biol.*, 196:901-917, (1987); Chothia et al., *Nature*, 342:878-883, (1989)).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an indiviCB1 variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the "AbM" definition and the contact definition.

The Kabat definition is a standard for numbering the residues in an antibody and is typically used to identify CDR regions. See e.g., Johnson & Wu, *Nucleic Acids Res.*, 28:214-8, (2000). The Chothia definition is similar to the Kabat definition, but the Chothia definition takes into account positions of certain structural loop regions. See e.g., Chothia et al., *J. Mol. Biol.*, 196:901-17, (1986); Chothia et al., *Nature*, 342:877-83, (1989). The "AbM" definition uses an integrated suite of computer programs produced by Oxford Molecular Group that model antibody structure. See e.g., Martin et al., *Proc. Natl. Acad. Sci.* (USA), 86:9268-9272, (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics, Suppl. 3:194-198, (1999). The contact definition is based on an analysis of the available complex crystal structures. See e.g., MacCallum et al., *J. Mol. Biol.*, 5:732-45, (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

Specificity of antibodies in various embodiments or fragments thereof, for CB1 receptors can be determined based on affinity and/or avidity. Affinity, represented by the equilibrium constant for the dissociation of an antigen with an antibody (Kd), measures the binding strength between an antigenic determinant and an antibody-binding site. Avidity is the measure of the strength of binding between an antibody with its antigen. Avidity is related to both the affinity between an epitope with its antigen-binding site on the antibody, and the valence of the antibody, which refers to the number of antigen-binding sites specific for a particular epitope. The lesser the value of the Kd, the stronger the binding strength between an antigenic determinant and the antibody binding site.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See e.g., Songsivilai et al., *Clin. Exp. Immunol.*, 79:315-321, (1990); Kostelny et al., *J. Immunol.*, 148:1547-1553, (1992).

Some species of mammals can also produce antibodies having only a single heavy chain.

Each individual CB1 immunoglobulin chain is typically composed of several "immunoglobulin domains." These domains are the basic units of which antibody polypeptides are composed. The heavy chain C region typically comprises one or more domains that can be responsible for effector function. The number of heavy chain constant region domains will depend on the isotype. The antibodies that are provided can have any of isotypes and subtypes.

The term "variable region" or "variable domain" refers to a portion of the light and/or heavy chains of an antibody. In certain embodiments, variable regions of different antibodies differ extensively in amino acid sequence even among antibodies of the same species. The variable region of an antibody typically determines specificity of a particular antibody for its target The term "neutralizing antigen-binding protein" or "neutralizing antibody" refers to an antigen-binding protein or antibody, respectively, that binds to a ligand and prevents or reduces the binding of the ligand to a binding partner. This can be done, for example, by directly blocking a binding site on the ligand or by binding to the ligand and altering the ligand's ability to bind through indirect means (such as structural or energetic alterations in the ligand). In some embodiments, the term can also denote an antigen-binding protein that prevents the protein to which it is bound from performing a biological function. In assessing the binding and/or specificity of an antigen-binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, about 20-30%, about 30-40%, about 40-50%, about 50-60%, about 60-70%, about 70-80%, about 80-85%, about 85-90%, about 90-95%, about 95-97%, about 97-98%, about 98-99% or more (as measured in an in vitro competitive binding assay). In some embodiments, in the case of CB1 receptor antigen-binding proteins, such a neutralizing molecule can diminish the binding ability of the receptor. In some embodiments, the neutralizing ability is characterized and/or described via a competition assay. In some embodiments, the neutralizing ability is described in terms of an $IC_{50}$ or $EC_{50}$ value. In some embodiments, the antigen-binding proteins may be non-neutralizing antigen-binding proteins.

The term "target" refers to a molecule or a portion of a molecule capable of being bound by an antigen-binding protein. In certain embodiments, a target can have one or more epitopes. In certain embodiments, a target is an antigen. The use of "antigen" in the phrase "antigen-binding protein" simply denotes that the protein sequence that comprises the antigen can be bound by an antibody. In this context, it does not require that the protein be foreign or that it be capable of inducing an immune response.

The term "compete" when used in the context of antigen-binding proteins (e.g., neutralizing antigen-binding proteins or neutralizing antibodies) that compete for the same epitope means competition between antigen-binding proteins as determined by an assay in which the antigen-binding protein (e.g., antibody or immunologically functional fragment thereof) being tested prevents or inhibits (e.g., reduces) specific binding of a reference antigen-binding protein (e.g., a ligand, or a reference antibody) to a common antigen (e.g., CB1 or a fragment thereof). Numerous types of competitive binding assays can be used to determine if one antigen-binding protein competes with another, for example: solid phase direct or indirect radioimmunoassay (RIA), solid phase direct or indirect enzyme immunoassay (EIA), sandwich competition assay (see e.g., Stahli, et al., 1983, *Methods in Enzymology,* 9:242-253); solid phase direct biotin-avidin EIA (see e.g., Kirkland, et al., 1986, *J. Immunol.,* 137:3614-3619) solid phase direct labeled assay, solid phase direct labeled sandwich assay (see e.g., Harlow and Lane, 1988, *Antibodies, A Laboratory Manual,* Cold Spring Harbor Press); solid phase direct label RIA using I-125 label (see e.g., Morel, et al., 1988, *Molec. Immunol.,* 25:7-15); solid phase direct biotin-avidin EIA (see e.g., Cheung, et al., 1990, *Virology,* 176:546-552); and direct labeled RIA (Moldenhauer et al., 1990, *Scand. J. Immunol.,* 32:77-82). Typically, such an assay involves the use of purified antigen bound to a solid surface or cells bearing either of these, an unlabelled test antigen-binding protein and a labeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins and antigen-binding proteins binding to an adjacent epitope sufficiently proximal to the epitope bound by the reference antigen-binding protein for steric hindrance to occur. Additional details regarding methods for determining competitive binding are provided in the examples herein. Usually, when a competing antigen-binding protein is present in excess, it will inhibit (e.g., reduce) specific binding of a reference antigen-binding protein to a common antigen by at least about 40-45%, about 45-50%, about about 50-55%, about 55-60%, about 60-65%, about 65-70%, about 70-75% or about 75% or more. In some instances, binding is inhibited by at least about 80-85%, about 85-90%, about 90-95%, about 95-97%, or about 97% or more.

The term "antigen" refers to a molecule or a portion of a molecule capable of being bound by a selective binding agent, such as an antigen-binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen-binding proteins, e.g., antibodies.

The term "epitope" includes any determinant capable of being bound by an antigen-binding protein, such as an antibody or to a T-cell receptor. An epitope is a region of an antigen that is bound by an antigen-binding protein that targets that antigen, and when the antigen is a protein, includes specific amino acids that directly contact the antigen-binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other indiviCB1 species in the same mixture. In certain embodiments, a substantially pure molecule is a composition wherein the object species comprises at least about 50% (on a molar basis) of all macromolecular species present. In other embodiments, a substantially pure composition will comprise at least about 80%, about 85%, about 90%, about 95%, or about 99% of all macromolecular species present in the composition. In other embodiments, the object species is purified to essential homogeneity wherein contaminating species cannot be detected in the composition by conventional detection methods and thus the composition consists of a single detectable macromolecular species. In various embodiments, the antigen binding protein can be a purified antigen binding protein or a purified antibody.

The term "biological sample," as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The terms "therapeutically effective amount" and "therapeutically effective dose" refer to the amount of a CB1 receptor antigen-binding protein determined to produce a therapeutic response in a mammal Such therapeutically effective amounts can be ascertained by one of ordinary skill in the art. The exact dose and formulation will depend on the purpose of the treatment, and will be ascertainable by one skilled in the art using known techniques (see e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy,* 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antigen-binding fragments, antibodies, peptibodies, carbohydrates or small organic molecules. An antibody can be made against CB1 CB1 receptors. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the specification. See e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Antigen-binding proteins that bind CB1 receptors, are provided herein. In some embodiments, the antigen-binding proteins provided are polypeptides which comprise one or more complementary determining regions (CDRs), as described herein. In some antigen-binding proteins, the CDRs are embedded into a "framework" region, which orients the CDR(s) such that the proper antigen-binding properties of the CDR(s) are achieved. In some embodiments, antigen-binding proteins provided herein can interfere with, block, reduce or modulate the CB1 receptors.

In some embodiments, the antigen-binding proteins provided herein are capable of inhibiting CB1-mediated activity e.g. ligand binding. In other embodiments, antigen-binding proteins binding to a CB1 receptor epitope can inhibit physiological effects mediated by the CB1 receptor. In some embodiments, the antigen-binding proteins are chimeras, such as a human/mouse chimera.

The antigen-binding proteins can be used in a variety of therapeutic applications. For example, to reduce body weight or improve metabolic parameters, e.g. plasma glucose, insulin, HDL cholesterol, triglyceride, adiponectin, and HbA1c levels, intraabdominal and liver fat, energy expenditure, and blood pressure In some embodiments, the antigen-binding proteins that are provided comprise one or more CDRs (e.g., 1, 2, 3, 4, 5 or 6 CDRs). In other embodiments, the antigen-binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature.

In certain embodiments, the polypeptide structure of the antigen-binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen-binding protein is an immunological fragment of an antibody (e.g., a Fab fragment, a Fab' fragment, a F(ab')$_2$ fragment, an Fv fragment, a diabody, or a single chain antibody molecule, such as an scFv)

In embodiments where the antigen-binding protein is used for therapeutic applications, an antigen-binding protein can inhibit, interfere with or modulate one or more biological activities of CB1. In one embodiment, an antigen-binding protein binds specifically to CB1 receptors and/or substantially inhibits binding or signaling of human CB1 receptors by at least about 20%-40%, about 40-60%, about 60-80%, about 80-85%, or more (for example, as measured in an in vitro assay).

Some of the antigen-binding proteins that are provided herein are antibodies. In some embodiments, the antigen-binding protein has a K$_d$ of less (binding more tightly) than about $10^{-7}$, about $10^{-8}$, about $10^{-9}$, about $10^{-10}$, about $10^{-11}$, about $10^{-12}$, about $10^{-13}$M. In some embodiments, the antigen-binding protein has an IC$_{50}$ for blocking the binding or signaling of CB1 receptors of less than about 1 µM, about 1000 nM to about 100 nM, about 100 nM to about 10 nM, about about 10 nM to about 1 nM, about 1000 pM to about 500 pM, about 500 pM to about 200 pM, less than about 200 pM, about 200 pM to about 150 pM, about 200 pM to about 100 pM, about 100 pM to about 10 pM, about 10 pM to about 1 pM.

In some embodiments, the antigen-binding proteins bind to a specific conformational state of CB1 receptors to prevent receptor activity.

As described herein, an antigen-binding protein to CB1 receptors can comprise a humanized antibody and/or part thereof. A practical application of such a strategy is the "humanization" of the mouse humoral immune system.

In certain embodiments, a humanized antibody is substantially non-immunogenic in humans. In certain embodiments, a humanized antibody has substantially the same affinity for a target as an antibody from another species from which the humanized antibody is derived. See e.g., U.S. Pat. No. 5,530,101; U.S. Pat. No. 5,693,761; U.S. Pat. No. 5,693,762; and U.S. Pat. No. 5,585,089.

In certain embodiments, amino acids of an antibody variable domain that can be modified without diminishing the native affinity of the antigen-binding domain while reducing its immunogenicity are identified. See e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies can be modified to eliminate glycosylation sites in order to increase affinity of the antibody for its cognate antigen. See e.g., Co et al., Mol. Immunol., 30:1361-1367, (1993). In certain embodiments, techniques such as "reshaping," "hyperchimerization," or "veneering/resurfacing" are used to produce humanized antibodies. See e.g., Vaswami et al., *Annals of Allergy, Asthma, & Immunol.*, 81:105, (1998); Roguska et al., *Prot. Engin.*, 9:895-904, (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., *J. Immunol.*, 62(6):3663-71, (1999).

In certain instances, humanizing antibodies can result in a loss of antigen-binding capacity. The humanized antibodies can then be "back mutated." In such embodiments, the humanized antibody can be mutated to include one or more of the amino acid residues found in the donor antibody. See e.g., Saldanha et al., *Mol. Immunol.*, 36:709-19, (1999).

In certain embodiments the complementarity determining regions (CDRs) of the light and heavy chain variable regions of an antibody to CB1 receptors can be grafted to framework regions (FRs) from the same, or another, species. In certain embodiments, the CDRs of the light and heavy chain variable regions of an antibody to CB1 receptors can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to CB1 receptor heavy chain or light chain are replaced with the FRs from a different heavy chain or light chain. In certain embodiments, rare amino acids in the FRs of the heavy and light chains of an antibody to CB1 receptors are not replaced, while the rest of the FR amino acids are replaced. Rare amino acids are specific amino acids that are in positions in which they are not usually found in FRs. In certain embodiments, the grafted variable regions from an antibody to CB1 receptors can be used with a constant region that is different from the constant region of an antibody to the CB1 receptors. In certain embodiments, the grafted variable regions are part of a single chain Fv antibody. CDR grafting is described, e.g., in U.S. Pat. Nos. 6,180,370; 6,054,297; 5,693,762; 5,859,205; 5,693,761; 5,565,332; 5,585,089; and 5,530,101, and in Jones, et al., *Nature*, 321:522-525, (1986); Riechmann et al., *Nature*, 332:323-327, (1988); Verhoeyen, et al., *Science*, 239:1534-1536, (1988), Winter, *FEBS Letts.*, 430:92-94, (1998), which are hereby incorporated by reference for any purpose.

In certain embodiments, antigen-binding proteins (such as antibodies) are produced by immunization with an antigen (e.g., CB1 receptors or a fragment thereof). The antibodies can be produced by immunization with full-length receptors, a soluble form of the receptors, the catalytic domains alone, the mature form of CB1 receptors, a splice variant form of the receptors, or a fragment thereof. In certain embodiments, the antibodies of can be polyclonal or monoclonal, and/or can be recombinant antibodies In certain embodiments, strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In other embodiments, amino acids in the framework regions of the variable domains can be targeted. Such framework regions have been shown to contribute to the target binding properties of certain antibodies. See e.g., Hudson, *Curr. Opin. Biotech.*, 9:395-402, (1999) and references therein.

In certain embodiments, smaller and more effectively screened libraries of antibody variants can be produced by restricting random or site-directed mutagenesis to hyper-mutation sites in the CDRs, which are sites that correspond to areas prone to mutation during the somatic affinity maturation process. See e.g., Chowdhury & Pastan, Nature Biotech., 17: 568-572, (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetrabase sequence comprising a purine (A or G), followed by guanine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

For preparation of suitable antibodies for various embodiments e.g., recombinant, monoclonal, or polyclonal antibodies, many techniques known in the art can be used (see e.g., Kohler & Milstein, *Nature*, 256:495-497, (1975); Kozbor et al., *Immunology Today*, 4:72, (1983); Cole et al., pp. 77-96 in *Monoclonal Antibodies and Cancer Therapy*, Alan R. Liss, Inc., (1985); Coligan, Current *Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see e.g., Kuby, *Immunol.*, (3$^{rd}$ ed. 1997)). Techniques for the production of single chain antibodies or recombinant antibodies (U.S. Pat. No. 4,946,778; U.S. Pat. No. 4,816,567) can be adapted to produce antibodies to polypeptides for various embodiments. Also, transgenic mice, or other organisms such as other mammals, may be used to express humanized or human antibodies (see e.g., U.S. Pat. Nos. 5,545,807; 5,545,806; 5,569,825; 5,625,126; 5,633,425; 5,661,016; Marks et al., *Bio/Technology*, 10:779-783, (1992); Lonberg et al., *Nature*, 368:856-859, (1994); Morrison, Nature, 368:812-13, (1994); Fishwild et al., *Nature Biotechnology*, 14:845-51, (1996); Neuberger, *Nature Biotechnology*, 14:826, (1996); and Lonberg & Huszar, *Intern. Rev. Immunol.*, 13:65-93, (1995)). Alternatively, phage display technology can be used to identify antibodies and heteromeric Fab fragments that specifically bind to selected antigens (see e.g., McCafferty et al., *Nature*, 348:552-554, (1990); Marks, et al., *Biotechnology*, 10:779-783, (1992)). Antibodies can also be made bispecific, i.e., able to recognize two different antigens (see e.g., WO 93/08829, Traunecker, et al., *EMBO J.*, 10:3655-3659, (1991); and Suresh, et al., *Methods in Enzymology*, 121:210, (1986)). Antibodies can also be heteroconjugates, e.g., two covalently joined antibodies, or immunotoxins (see e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see e.g., Jones, et al., *Nature*, 321:522-525, (1986); Riechmann et al., *Nature*, 332:323-327, (1988); Verhoeyen, et al., *Science*, 239:1534-1536, (1988) and Presta, *Curr. Op. Struct. Biol.* 2:593-596, (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In an alternative approach, others, including GenPharm International, Inc., have utilized a "minilocus" approach. In the minilocus approach, an exogenous Ig locus is mimicked through the inclusion of pieces (indiviCB1 genes) from the Ig locus. Thus, one or more $V_H$ genes, one or more $D_H$ genes, one or more $J_H$ genes, a mu constant region, and usually a second constant region (e.g. a gamma constant region) are formed into a construct for insertion into an animal. This approach is described in U.S. Pat. No. 5,545,807 to Surani, et al. and U.S. Pat. Nos. 5,545,806; 5,625,825; 5,625,126; 5,633,425; 5,661,016; 5,770,429; 5,789,650; 5,814,318; 5,877,397; 5,874,299; and 6,255,458 each to Lonberg & Kay, U.S. Pat. Nos. 5,591,669 and 6,023,010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. Nos. 07/574,748; 07/575,962; 07/810,279; 07/853,408; 07/904,068; 07/990,860; 08/053,131; 08/096,762; 08/155,301; 08/161,739; 08/165,699; 08/209,741, the disclosures of which are hereby incorporated by reference. See also, European Patent No. 0 546 073 B1, International Patent Application Nos.: WO 92/03918; WO 92/22645; WO 92/22647; WO 92/22670; WO 93/12227; WO 94/00569; WO 94/25585; WO 96/14436; WO 97/13852; and WO 98/24884, and U.S. Pat. No. 5,981,175, the disclosures of which are hereby incorporated by reference in their entirety. See further, Taylor, et al., 1992, Chen, et al., 1993; Tuaillon, et al., 1993; Choi, et al., 1993, Lonberg, et al., (1994); Taylor, et al., (1994), and Tuaillon, et al., (1995), Fishwild, et al., (1996), the disclosures of which are hereby incorporated by reference.

In one embodiment, the antibody is conjugated to an "effector" moiety. The effector moiety can be any number of molecules, including labeling moieties such as radioactive labels or fluorescent labels, or can be a therapeutic moiety.

The antibodies can be fused to additional amino acid residues. Such amino acid residues can be a peptide tag, perhaps to facilitate isolation. Other amino acid residues for homing of the antibodies to specific organs or tissues are also contemplated.

In certain embodiments the antibody or the antigen-binding region of any of the monoclonal antibodies described herein can be used to treat cancer or retinopathy.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216; 4,912,040; 4,740,461; and 4,959,455, (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels of the antibody of interest.

In certain embodiments, antigen-binding proteins can comprise an immunoglobulin molecule of at least one of the IgG1, IgG2, IgG3, IgG4, Ig E, IgA, IgD, and IgM isotype. In certain embodiments, antigen-binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen-binding proteins have been cloned for expression in mammalian cells. In certain embodiments, antigen-binding proteins comprise a constant region other than any of the constant regions of the IgG1, IgG2, IgG3, IgG4, IgE, IgA, IgD, and IgM isotype.

In certain embodiments, substantial modifications in the functional and/or chemical characteristics of antibodies to CB1 receptors can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a nonnative residue such that there is little or no effect on the polarity or charge of the amino acid residue at that position. Furthermore, any native residue in the polypeptide can also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to CB1 receptors, or to increase or decrease the affinity of the antibodies to CB1 receptors as described herein.

In certain embodiments, antibodies or antigen-binding proteins can be expressed in cell lines other than hybridoma cell lines. Sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216; 4,912,040; 4,740,461; and 4,959,455, (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen-binding proteins comprise one or more polypeptides. Any of a variety of expression vector/host systems can be utilized to express polynucleotide molecules encoding polypeptides comprising one or more antigen-binding protein components or the antigen-binding protein itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more antigen-binding protein components or the antigen-binding protein itself is recombinantly expressed in yeast. Certain such embodiments use commercially available expression systems, e.g., the *Pichia Expression System* (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more antigen-binding protein components or the antigen-binding protein itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more antigen-binding protein components or the antigen-binding protein itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more antigen-binding protein components or the antigen-binding protein itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia* larvae. See e.g., Smith, et al., *J. Virol.*, 46: 584, (1983); Engelhard et al., *Proc. Nat. Acad. Sci.* (USA), 91: 3224-7, (1994).

In certain embodiments, polypeptides comprising one or more antigen-binding protein components or the antigen-binding protein itself made in bacterial cells are produced as insoluble inclusion bodies in the bacteria. Host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, M.O.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of $Mg^{++}$ and $Ca^{++}$. In certain embodiments, the polypeptide is further purified by fractionating the resuspended pellet in a denaturing SDS polyacrylamide gel (see e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more antigen-binding protein components or the antigen-binding protein itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more antigen-binding protein components or the antigen-binding protein itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromatography (HPLC). In certain embodiments, purification steps can be changed or certain steps can be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more antigen-binding protein components or the antigen-binding protein itself is partially purified. Partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See e.g., Capaldi, et al., Biochem. *Biophys. Res. Comm.*, 76: 425, (1977). It will be appreciated that under different electrophoresis conditions, the apparent molecular weights of purified or partially purified polypeptide can be different.

In various embodiments described herein, antibodies can be used in vivo and in vitro for investigative or diagnostic methods, which are well known in the art. The diagnostic methods include kits, which contain antibodies in various embodiments. In other embodiments the antibodies described herein can be used as a therapeutic.

It is understood that the CB1-receptor antibodies, where used in a mammal for the purpose of prophylaxis or treatment, can be administered in the form of a composition that additionally can comprise a pharmaceutically acceptable carrier. Suitable pharmaceutically acceptable carriers include, for example, one or more of water, saline, phosphate buffered saline, dextrose, glycerol, ethanol and the like, as well as combinations thereof.

Pharmaceutically acceptable carriers can further comprise minor amounts of auxiliary substances such as wetting or emulsifying agents, preservatives or buffers, which enhance the shelf life or effectiveness of the antigen-binding proteins. The compositions of the injection can, as is well known in the art, be formulated so as to provide quick, sustained or delayed release of the active ingredient after administration to the mammal Pharmaceutical formulations, particularly, of the antibodies for use described herein can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants. The antibody can be formulated at a concentration of between 0.5-200 mg/ml.

In therapeutic applications, compositions are administered to a patient suffering from a disease (e.g., a muscle wasting disease) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" as referred to herein can include both humans and other animals, particularly mammals. Thus the methods are applicable to both human therapy and veterinary applications. In various embodiments the patient is a mammal. The mammal can be a primate, or even a human.

The route of administration of a pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired CB1 receptor antigen-binding protein to CB1, with or without additional therapeutic agents, in a pharmaceutically acceptable vehicle. In certain embodiments, a vehicle for parenteral injection is sterile distilled water in which a CB1 receptor antigen-binding protein to CB1 receptors, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

Uses of Cb1 Receptor Antigen Binding Compositions

The present invention provides methods and pharmaceutical compositions for inhibiting, reducing or neutralizing the amount or activity of the CB1 receptor.

In one aspect, the present invention provides methods and reagents for treating CB1 related disorders in a subject in need of such a treatment by administering an effective dosage of a CB1 receptor antigen binding protein composition to the subject. As used herein the term "subject" refers to any animal, such as mammals including humans.

The disorders that can be treated by a CB1 receptor antigen binding protein composition include but are not limited to various metabolic disorders such as diabetes and related disorders.

Administering the antigen binding proteins described herein may improve plasma glucose or lipid levels. Therefore, administering the compositions disclosed herein may improve diabetes, obesity or hyperglycemic conditions in suitable subjects. In addition, compositions containing the antigen binding protein may decrease food intake in individuals.

Other aspects of the invention will be appreciated by one skilled in the art, and are described herein. Although various embodiments of the invention have been described herein, including the following examples, those skilled in the art will readily appreciate that the specific examples and studies detailed herein are only illustrative. It should be understood that various modifications can be made without departing from the spirit of the invention.

EXAMPLES

The following sequences are relevant to this application:

TABLE 2

| SEQ ID NO: | DESCRIPTION |
|---|---|
| 1 | Human CB1 receptor |
| 2 | Mouse CB1 receptor |
| 3 | Rat CB1 receptor |
| 4 | Ab HC |
| 5 | Ab LC |
| 6 | Mutated HC |
| 7 | Mutated HC |
| 8 | Mutated LC |
| 9 | Mutated LC |
| 10 | Mutated LC |
| 11 | Mutated LC |
| 12 | Mutated LC |
| 13 | Mutated LC |
| 14 | Mutated LC |
| 15 | Mutated LC |
| 16 | Mutated LC |
| 17 | HC CDR1 |
| 18 | HC CDR2 |
| 19 | HC CDR3 |
| 20 | LC CDR1 |
| 21 | LC CDR2 |
| 22 | LC CDR3 |
| 23 | HC FR1 |
| 24 | HC FR2 |
| 25 | HC FR3 |
| 26 | HC CDR2 |
| 27 | HC FR3 |
| 28 | LC FR1 |
| 29 | LC FR2 |
| 30 | LC FR3 |
| 31 | 10D10 mutant LC |
| 32 | 10D10 mutant LC |
| 33 | 10D10 mutant LC |
| 34 | 10D10 mutant LC |
| 35 | 10D10 mutant LC |
| 36 | 10D10 mutant LC |
| 37 | 10D10 mutant HC |
| 38 | 10D10 mutant HC |
| 39 | 10D10 mutant LC |
| 30 | 10D10 mutant LC |
| 40 | 10D10 mutant LC |
| 41 | 10D10 mutant LC |
| 42 | 10D10 mutant HC |
| 43 | 10D10 mutant HC |
| 44 | 10D10 mutant HC |
| 45 | 10D10 mutant HC |
| 46 | 10D10 mutant HC |
| 47 | 10D10 mutant HC |
| 48 | 10D10 mutant HC |

Example 1

Antibody Generation

Multiple antibody campaigns were conducted. In the first campaign 41 CB1 binders were identified, including the antagonist 10D10 of human CB1 In the second campaign, 507 CB1 binders were obtained, however none were antagonists of CB1. In the third campaign 58 CB1 binders were identified and all were antagonists of human CB1. None of the CB1 binding antibodies were antagonists to mouse CB1

The CB1 antibody 10D10 was generated by immunizing Xenomouse strains XMG2/K and XMG4/KL with transiently transfected HEK 293 cells expressing PADRE-hCB1 and E3K-hCB1 Immune cell tissues from mice showing positive titers were harvested, pooled and used to generate hybridomas. Hybridoma supertants containing hCB1-binding antibodies were identified by FACS analysis using hCB1-expressing CHO cells, and antagonist activity evaluated using the hCB1 cAMP assay.

Antibody 10D10 was obtained and characterized. Sequences of the heavy chain, light chain, CDR's and framework regions are provided below.

```
10D10 HC
                                            (SEQ ID NO: 4)
QVQLQESGPGLVKPSQTLSLTCTVSGGSIRRGGDYWSWIRQHPGKGLEW

IGYIYYSGSTNYNPSLKSRATISVDTSKNQFSLKLSSVTAADTAVYYCA

RDYDILTGYSYYYYGMDVWGQGTTVTVSSASTKGPSVFPLAPCSRSTSE

STAALGCLVKDYFPEPVTVSWNSGALTSGVHTFPAVLQSSGLYSLSSVV

TVPSSNFGTQTYTCNVDHKPSNTKVDKTVERKCCVECPPCPAPPVAGPS

VFLFPPKPKDTLMISRTPEVTCVVVDVSHEDPEVQFNWYVDGVEVHNAK

TKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQ

PENNYKTTPPMLDSDGSFFLYSKLTVDKSRWQQGNVFSCSVMHEALHNH

YTQKSLSLSPGK

10D10 LC
                                            (SEQ ID NO: 5)
DIVMTQSPLSLPVTPGEPASISCRSSQSLLHSNGYNYLDWYLQKPGQSP

QLLIYLGSNRASGVPDRFSGSGSGTDFTLKIRRVEAEDVGVYYCMQALQ

TPRTFGQGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

The sequences of the CDRs and framework regions for 10D10 follow:

```
CDR Sequences
HC-CDR1     RGGDYWS (SEQ ID NO: 17)

HC-CDR2     YIYYSGSTNYNPSLKS (SEQ ID NO: 18)

HC-CDR3     DYDILTGYSYYYYGMDV (SEQ ID NO: 19)

LC-CDR1     RSSQSLLHSNGYNYLD (SEQ ID NO: 20)

LC-CDR2     LGSNRAS (SEQ ID NO: 21)

LC-CDR3     MQALQTPRT (SEQ ID NO: 22)

Framework Sequences
HC-FR1      QVQLQESGPGLVKPSQTLSLTCTVSGGSIR
            (SEQ ID NO: 23)

HC-FR2      WIRQHPGKGLEWIG (SEQ ID NO: 24)

HC-FR3      RATISVDTSKNQFSLKLSSVTAADTAVYYCAR
            (SEQ ID NO: 27)

LC-FR1      DIVMTQSPLSLPVTPGEPASISC (SEQ ID NO: 28)

LC-FR2      WYLQKPGQSPQLLIY (SEQ ID NO: 29)

LC-FR3      GVPDRFSGSGSGTDFTLKIRRVEAEDVGYYC
            (SEQ ID NO: 30)
```

Framework and CDR regions of the HC and LC for several additional antibodies are provided in FIGS. 2A-2B. These are HC FR1 (SEQ ID NO: 23), HC FR2 (SEQ ID NO: 24) and HC FR3 (SEQ ID NO: 27). Related HC CDR1 (SEQ ID NO: 17), HC CDR2 (SEQ ID NO: 26—YI-YYSGSTYYNPSLKS) and HC CDR3 (SEQ ID NO: 19) sequences are also provided in this figure. Also shown are the related LC CDR1 (SEQ ID NO: 20), LC CDR2 (SEQ ID NO: 21) and LC CDR 3 (SEQ ID NO: 22). One of skill in the art interpreting the figure would realize that they would start with the sequences of 1A11 and make the indicated amino acid changes to arrive at the sequence of the additionally described antibodies The CDR regions of the heavy and light chains of the antibody were mutagenized and additional antigen-binding proteins were obtained. Single amino acid residue randomized mutagenesis (NNK codon) (N=A, T, G, or C; K=T or G) was performed on every residue in all three HC-CDRs and all three LC-CDRs above (SEQ ID NOs: 17-22).

Mutagenesis primers were designed by flanking NNK with 24 wild type nucleotides 5-prime and 24 wild type nucleotides 3-prime to the targeted position. 40 positions in HC-CDRs and 32 positions in LC-CDRs were mutated. A total of 1368 mutants were generated.

Plasmid DNA containing 10D10 heavy chain and plasmid DNA containing 10D10 light chain in pTTS vector were used as the template for mutagenesis reactions. CB1 mutants were identified by sequencing and isolated. Single residue mutants were created by pairing every mutant of the light chain with the wild type heavy chain, and every mutant of the heavy chain with the wild type light chain. Conditioned media (CM) were harvested on 7th day after transfection and used in cell based ELISA for binding assessment.

Two to four beneficial mutations in a CDR were combined using specific mutagenesis primers to generate complex site-directed mutants (CSDM). CSDM with further improved affinity were identified by FACS at 0.1 ug/mL antibody concentration. Pairing of CSDM mutant LC and CSDM mutant HC resulted in additional affinity improvement. N35Y mutation was added to the CSDM mutant LC using specific mutagenesis primer to improved the biochemical properties of CSDM mutants.

The following LC and HC mutants based on 10D10 were obtained and their sequences are presented below.

```
10D10-D83K HC
                                            (SEQ ID NO: 6)
QVQLQESGPGLVKPSQTLSLTCTVSGGSIRRGGDYWSWIRQHPGKGLEWI

GYIYYSGSTNYNPSLKSRATISVKTSKNQFSLKLSSVTAADTAVYYCARD

YDILTGYSYYYYGMDVWGQGTTVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS

PGK

10D10-31Y HC, 10D10-41Y HC, 10D10-43Y HC (H2-1)
                                            (SEQ ID NO: 7)
QVQLQESGPGLVKPSQTLSLTCTVSGGSIRRGGDYWSWIRQHPGKGLEWI

GYIYYSGSTLYNPRLKSRATISVDTSKNQFSLKLSSVTAADTAVYYCARD

YDILTGYSYYYYGMDVWGQGTTVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE
```

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS

PGK

10D10-31Y LC (L1-8Y)
(SEQ ID NO: 8)
DIVMTQSPLSLPVTPGEPASISCRSSQSLYHSYGYNYLDWYLQKPGQSPQ

LLIYLGSNRASGVPDRFSGSGSGTDFTLKIRRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-31Y R94S LC (L1-8Y R94S)
(SEQ ID NO: 9)
DIVMTQSPLSLPVTPGEPASISCRSSQSLYHSYGYNYLDWYLQKPGQSPQ

LLIYLGSNRASGVPDRFSGSGSGTDFTLKISRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-41Y LC (L2-1Y)
(SEQ ID NO: 10)
DIVMTQSPLSLPVTPGEPASISCRSSQSLLHSYGYNYLDWYLQKPGQSPQ

LLIYLGYKKASGVPDRFSGSGSGTDFTLKIRRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-41Y R94S LC (L2-1Y R94S)
(SEQ ID NO: 11)
DIVMTQSPLSLPVTPGEPASISCRSSQSLLHSYGYNYLDWYLQKPGQSPQ

LLIYLGYKKASGVPDRFSGSGSGTDFTLKISRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-43Y LC (L3-2Y)
(SEQ ID NO: 12)
DIVMTQSPLSLPVTPGEPASISCRSSQSLLHSYGYNYLDWYLQKPGQSPQ

LLIYLGSNRASGVPDRFSGSGSGTDFTLKIRRVEAEDVGVYYCMQARGT

VRTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

10D10-43Y R94S LC (L3-2Y R94S)
(SEQ ID NO: 13)
DIVMTQSPLSLPVTPGEPASISCRSSQSLLHSYGYNYLDWYLQKPGQSPQ

LLIYLGSNRASGVPDRFSGSGSGTDFTLKISRVEAEDVGVYYCMQARGTV

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-LYYY-5 LC (L1YYY-5)
(SEQ ID NO: 14)
DIVMTQSPLSLPVTPGEPASISCRSSQSLLHYYGYNYLDWYLQKPGQSPQ

LLIYLGSNRASGVPDRFSGSGSGTDFTLKIRRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-LYYY-5 R94S LC (L1YYY-5 R94S)
(SEQ ID NO: 15)
DIVMTQSPLSLPVTPGEPASISCRSSQSLLHYYGYNYLDWYLQKPGQSPQ

LLIYLGSNRASGVPDRFSGSGSGTDFTLKISRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-N35Y LC (N35Y)
(SEQ ID NO: 16)
DIVMTQSPLSLPVTPGEPASISCRSSQSLLHSYGYNYLDWYLQKPGQSPQ

LLIYLGSNRASGVPDRFSGSGSGTDFTLKIRRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Various combinations of mutated HC and LC were made. The combinations are described in Table 3.

TABLE 3

| Matured mutant | LC name | HC name | Mutation location in LC AHO # | Mutation location in HC AHO # |
|---|---|---|---|---|
| N35W | N35W | WT HC | N35W | none |
| 8Y | L1-8Y | WT HC | L32Y, N35Y | none |
| 31Y | L1-8Y | H2-1 | L32Y, N35Y | N69L, S73R |
| 41Y | L2-1Y | H2-1 | N35Y, S68Y, N69K, R70K | N69L, S73R |
| 43Y | L3-2Y | H2-1 | N35Y, L110R, Q111G, P136V | N69L, S73R |
| D83K/N35Y | N35Y | D83K | N35Y | D83K |
| LYYY-5 | L1YYY-5 | WT HC | S34Y, N35Y | none |
| D83R | WT LC | D83R | none | D83R |

Characteristics of top affinity maturated antibodies are shown in FIG. 3.

FIG. 2 provides information concerning binders from the first campaign. The figure presents the framework and CDR sequence of the HC and LC. It will be noted that the sequence diversity is not great between the different antibodies. Looking at FIGS. 2A and 2B, one of ordinary skill in the art would recognize that substitutions of one to eight amino acids can be made in the sequence presented for 1A11 in order to obtain the additional antibodies disclosed in the figure. Any of these antibodies can be encompassed in various embodiments of the disclosure.

Covariance analysis to suggests further changes to the antibodies. These suggested changes are shown below in Tables 4 and 5.

TABLE 4

COVARIANCE ANALYSIS SUGGESTS CHANGES FOR THE 31Y, 41Y, 43Y AND LYYY-5 VARIANTS

41-Y

| | | | |
|---|---|---|---|
| 1. | 001 | 10D10CSDM-41Y_heavy: | [T144L] |
| 2. | 002 | 10D10CSDM-41Y_kappa: | [R94S], 10D10CSDM-41Y_heavy: [T144L] |
| 3. | 003 | 10D10CSDM-41Y_kappa: | [R94S] |
| 4. | 004 | 10D10CSDM-41Y_kappa: | [R94S], 10D10CSDM-41Y_heavy: [Q17E] |
| 5. | 005 | 10D10CSDM-41Y_heavy: | [H47P] |
| 6. | 006 | 10D10CSDM-41Y_kappa: | [R94S], 10D10CSDM-41Y_heavy: [Q17E, H47P] |
| 7. | 007 | 10D10CSDM-41Y_kappa: | [R94S], 10D10CSDM-41Y_heavy: [Q17E, H47P, T144L] |
| 8. | 008 | 10D10CSDM-41Y_kappa: | [R94S], 10D10CSDM-41Y_heavy: [Q17E, R23S, H47P, T144L] |
| 9. | 009 | 10D10CSDM-41Y_kappa: | [R94S], 10D10CSDM-41Y_heavy: [Q17E, R23S, H47P] |
| 10. | 010 | 10D10CSDM-41Y_heavy: | [Q17E, H47P] |

TABLE 5

ADDITIONAL COVARIANCE ANALYSIS SUGGESTS CHANGES FOR THE N35Y/D83K AND D83R VARIANTS

| | | | |
|---|---|---|---|
| 1. | 001 | 10D10D83R_heavy: | [T144L] |
| 2. | 002 | 10D10D83R_kappa: | [R94S], 10D10D83R_heavy: [T144L] |
| 3. | 003 | 10D10D83R_kappa: | [R94S] |
| 4. | 004 | 10D10D83R_kappa: | [R94S], 10D10D83R_heavy: [Q17E] |
| 5. | 005 | 10D10D83R_heavy: | [H47P] |
| 6. | 006 | 10D10D83R_kappa: | [R94S], 10D10D83R_heavy: [Q17E, H47P] |
| 7. | 007 | 10D10D83R_kappa: | [R94S], 10D10D83R_heavy: [Q17E, H47P, T144L] |
| 8. | 008 | 10D10D83R_kappa: | [R94S], 10D10D83R_heavy: [Q17E, R23S, H47P, T144L] |
| 9. | 009 | 10D10D83R_kappa: | [R94S], 10D10D83R_heavy: [Q17E, R23S, H47P] |
| 10. | 010 | 10D10D83R_heavy: | [Q17E, H47P, K86D] |
| 11. | 011 | 10D10D83R_kappa: | [R94S], 10D10D83R_heavy: [K86D] |

Example 2

Antibody Characteristics

Several different antibodies were characterized using different assays to investigate characteristics of the CB1 receptor antibodies. An exemplary antibody, 10D10, is a Xenomouse antibody (i.e. a human antibody) that is functional in cAMP, aequorin and GTP-Eu assays. Results from these assays show that the antibody antagonizes synthetic (CP 55,940) and endogenous (anandamide) agonists and binds to the epitope represented by EC2 domain region in FIG. 1.

Figure 4A:
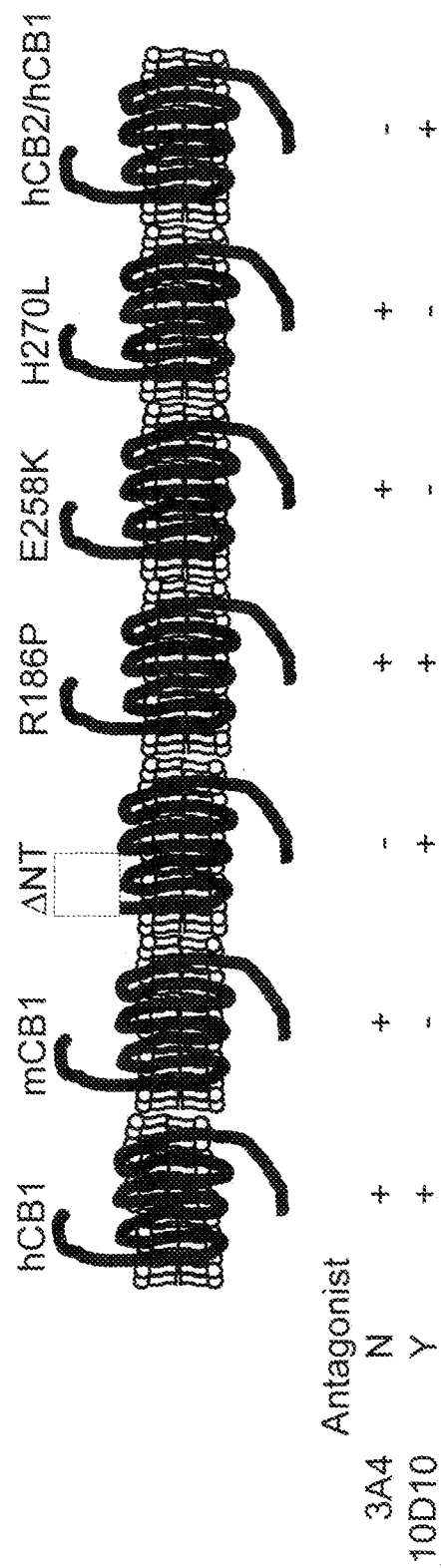

Results of binding of 10D10 and another antibody, 3A4, which is not an antagonist, to wild type and mutated CB1 receptor sequences is summarized in FIG. 4A. Cartoon drawings are used to represent the different mutant CB1 receptors used in the analysis. They include wild-type human CB1 (hCB1), wild-type mouse CB1 (mCB1), human CB1 that does not contain the extracellular N-terminus (ΔNT), human CB1 receptors containing single amino acid substitutions in EC1 (R186P) and EC2 (E258K and H270L), and human CB2 containing the three extracellular loops of human CB1 (hCB2/hCB1).

It can be seen that 10D10 does not bind or antagonize if there are mutations in the EC2 domain region (E258K and H270L) or if CB1 has the mouse sequence, however it still antagonizes if a mutations is made in the EC1 domain region (R186P). 10D10 will also bind and antagonize a mutated CB1 receptor that does not contain the extracellular N-terminus. Contrary to this, the 3A4 antibody will still bind and not antagonize despite mutation in either the EC1 or EC2 domains of CB1, but it does not bind to the mutated CB1 receptor that does not contain the extracellular N-terminus FIG. 4B shows binding of CB1 antibodies to cells transfected with various receptor constructs in a FACS assay. Receptor expression is documented by antibodies raised against epitope tags (e.g., V5 or E3K) present on the N-terminus of each receptor. Receptors used in the study are wild-type mouse CB1 (V5-mCB1), wild-type human CB1 (V5-hCB1), human CB1 that does not contain the extracellular N-terminus (E3K-hCB1 del.NT), human CB2 containing the three extracellular loops of human CB1 (V5-hCB2/hCB1 ECL1-3), three human CB1 receptors containing single amino acid substitutions in EC1 (V5-hCB1 R186P) and EC2 (V5-hCB1 E258K and V5-hCB1 H270L). Cells were probed either with no antibody (Un), a control antibody (IgG-PE), an anti-V5 antibody (V5), an anti E3K antibody (E3K), and various anti-CB1 antibodies (3A4, 3H7, 10B4, 10D2, 10D10, 1A11, 1E9, and 5G4). Highlighted squares indicate positive signal in the assay. It should be noted that 10B4 and 10D2 do not appear to show binding. This could be due to low Ab concentrations or loss of binding activity when the clones were grown up.

Figure 4C:
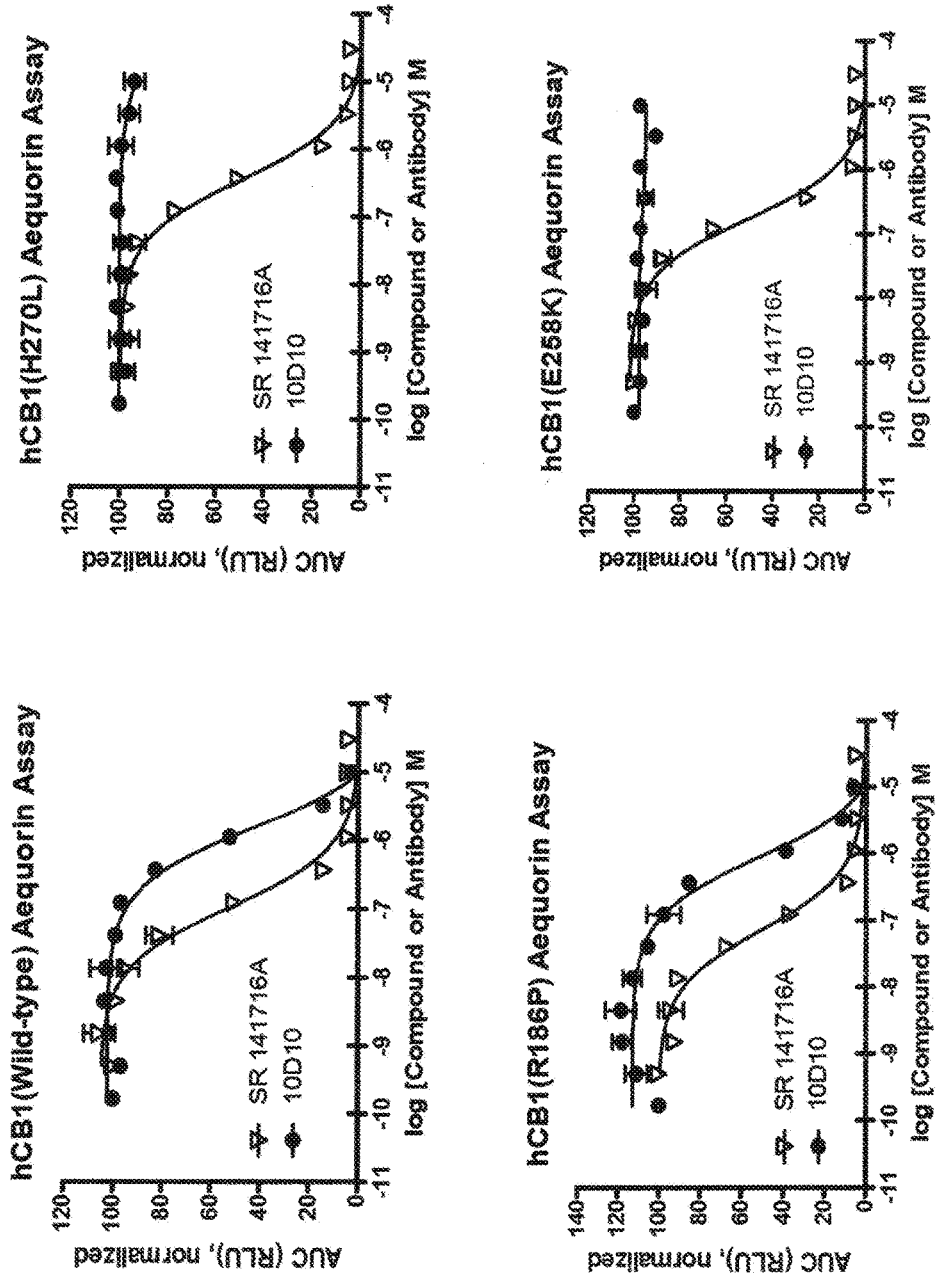

FIG. 4C shows that binding of 10D10 to CB1 is required for antagonist activity. The data shown are from an aequorin assay. The positive control, the small molecule antagonist SR 141716A, is active on wild-type CB1, hCB1 R186P, hCB1 H270L, and hCB1 E258K. 10D10 only shows antagonist activity on wild-type CB1 and hCB1 R186P, to which it binds, and not hCB1 H270L and hCB1 E258K, to which it does not bind.

Assays used to characterize the antibodies are described below.

GTP-Eu Assay

The GTP-Eu assay was performed using reagents DELFIA GTP-Eu Reagents, DELFIA GTP-binding Buffers, and hCB1 membranes from PerkinElmer. Antagonist activity was determined in 96-well Pall ArcoWell filtration plates by pre-incubating antagonists with 4.5 ug/well membrane, 50 ug/well Saponin, 150 mM NaCl, 10 mM MgCl2, 10 nM GTP-Eu, 5 uM GDP, 0.1% BSA, 50 mM HEPES, for 15 minutes followed by addition of 600 nM (FIG. 6A) or a dose response (FIG. 6B) of the CB1 agonist anandamide for 45 minutes. Plates were washed twice with GTP wash buffer using a Millipore manifold and read on a Victor reader.

cAMP Assay

CHO cells stably expressing hCB1 (Euroscreen) were grown in DMEM containing 10% FBS, 1% Pen/Strep/L-glutamine, 25 mM Hepes, 0.1 mM NEAA, 1 mM sodium pyruvate, and 400 ug/ml G418. To determine antagonist activity, cells were seeded in 96-well plates at a density of 10,000 cells per well in 80 ul DMEM containing 0.5% FBS, 1% Pen/Strep/L-glutamine, 25 mM Hepes, 0.1 mM NEAA, 1 mM sodium pyruvate, and 400 ug/ml G418. After overnight incubation, media was replaced with 5 µl fresh media and then 5 µl forskolin and CP 55-940 in media were added, followed by 40 µl of antibody. The final concentrations of forskolin and CP 55,940 were 15 µM and 250 pM, respectively. Antibodies were diluted in 10 mM NaAcetate pH5.0, 150 mM NaCl. The forskolin/CP 55,940/antibody mixture was left on the cells for 30 minutes at 37° C., and then it was removed and cAMP levels were measured using a DiscoverX XS+ cAMP assay kit following the manufacturer's protocol. Plates were read for 30 seconds on PerkinElmer ViewLux Microplate Imager.

Aequorin Assay

CHOK1 cells grown in DMEM/F12 containing 10% FBS were plated in 10 cm dishes at 5×106 cells/dish and then transiently transfected with plasmids encoding CB1, Ga16 and Aequorin in a 2:1:10 ratio using Lipofectamine 2000 in Opti-Mem. After overnight incubation, the cells were trypsinized and resuspended in 10 ml aequorin buffer containing HBSS, 20 mM HEPES, 0.01% Fatty acid free BSA and 10 ul coelenterazine (1 ug/ul), transferred to a foil-covered beaker and stirred gently at room temperature for 2 hrs. Cells were dispensed onto pre-warmed (37° C.) assay plates containing antibodies at twice the final concentration and 60 nM CP 55,940. using a Microlumat. Typically, 100 ul of cells were added to 100 ul of test article. Kinetic reads were performed for 20s, and the area under the curve from 2-20s was used to generate the dose response curves.

KinExa Assay 100 pM antibody was incubated with $1\times10^6$, $3\times10^6$, and $9\times10^6$ cell/ml of CHO35 cells expressing huCB1 in DMEM/F12 containing 1% FBS and 0.05% sodium azide, and samples were rocked for 4 hours at room temperature. Unbound free antibody was separated from whole cells and antibody-cell complexes using a Beckman GS-6R centrifuge at approximately 220×g for 5 min. The supernatant was filtered through a 0.22 µm filter and then passed over goat-anti-huFc-coated UltraLink Biosupport resin. The amount of the bead-bound Ab was quantified by fluorescent labeled anti-huIgG (H+L) antibody. The binding signal is proportional to the concentration of free Ab in solution at each cell density. The relative binding signal 100% represents 100 pM antibody alone. The decreased signal indicates the antibody binding with cells.

The 10D10 antibody does not recognize mouse CB1 (SEQ ID NO: 2) and has an affinity for hCB1 of less than 200 nM. Subsequent in vitro maturation efforts have yielded additional, more potent (~4-6×) antibodies that also antagonize signaling of the human CB1 receptor. Examples of these antibodies N35Y/D83K, 41Y, 43Y, LYYY-5.

Figure 5B:
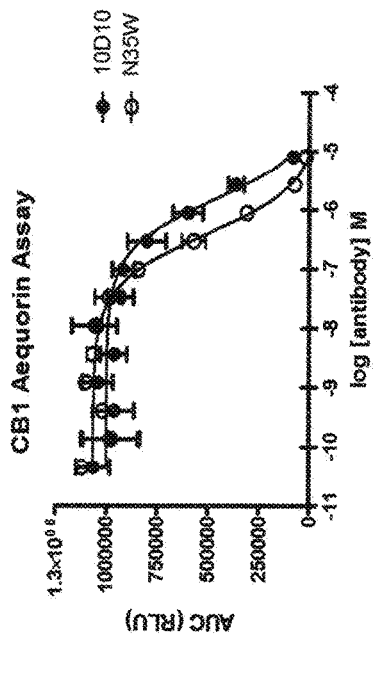
FIGS. 5A-5C presents activity of CB1 antagonist antibodies in cAMP (FIG. 5A), Aequorin (FIG. 5B) signaling assays and KinExA (FIG. 5C) binding assay.
Figure 5A:
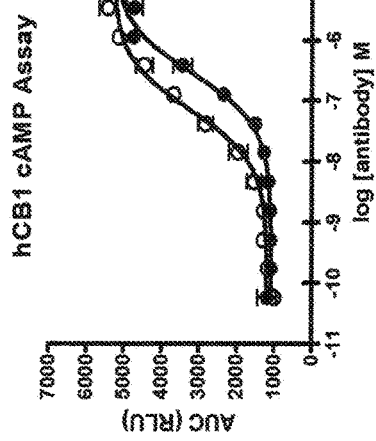
Figure 5C:
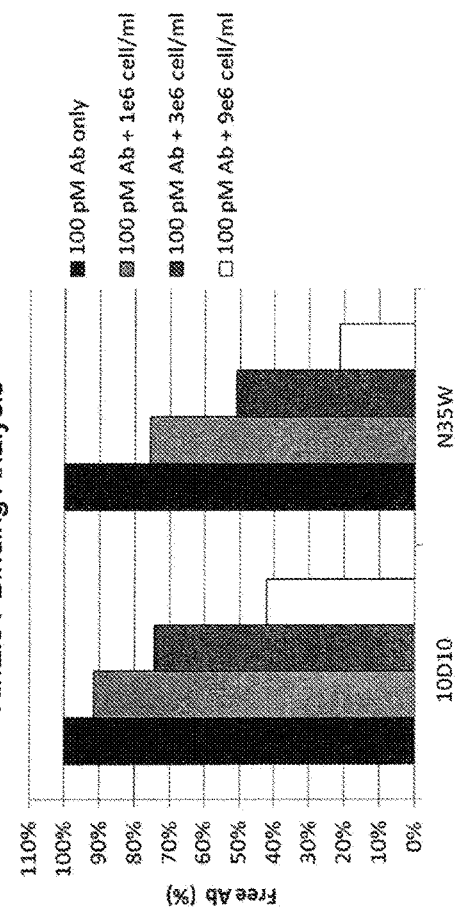

N35W is an affinity maturated antagonistic CB1 antibody based on 10D10 that is approximately 4-fold more potent than 10D10. This is shown in FIGS. 5A-5C. In 5A, the $EC_{50}$ of N35W is $6.973\times10^{-8}$ vs $2.826\times10^{-7}$ for 10D10 in a cAMP assay. It can also be seen that cAMP levels increase as both 10D10 and N35W concentrations increase. In the Aequorin assay (FIG. 5B), the $EC_{50}$ of N35W is $3.878\times10^{-7}$ vs $1.520\times10^{-6}$ for 10D10 and increasing amounts of the antibodies show a decrease in the area under the curve. In both figures, increasing amounts of the antibodies demonstrate inhibition of CB1.

KinExA binding analysis (FIG. 5c) shows that more N35W than 10D10 binds to CB1-expressing CHO cells (as indicated by less free antibody after incubation), signifying higher binding affinity of N35W compared to 10D10.

Figure 6A:
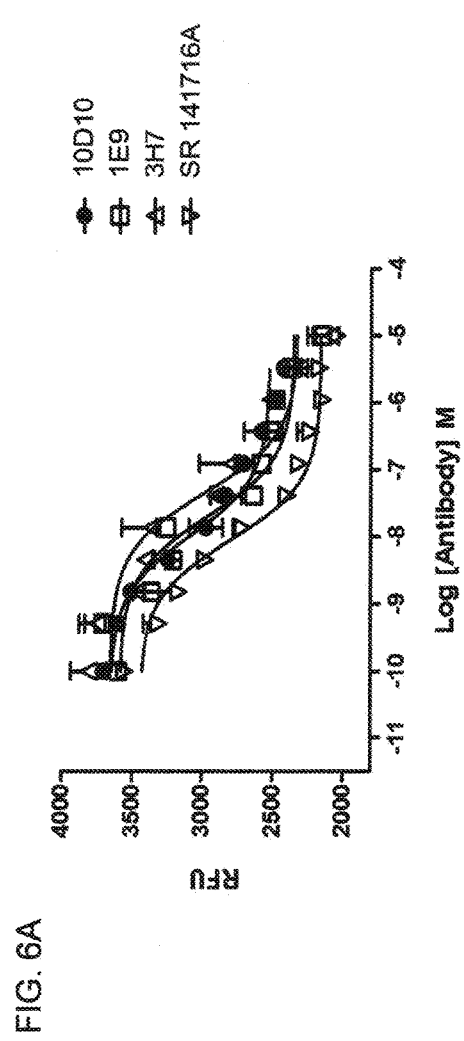
FIG. 6A presents activity of CB1 antagonist antibodies in a GTP-Eu assay compared to anandamide.
Figure 6B:
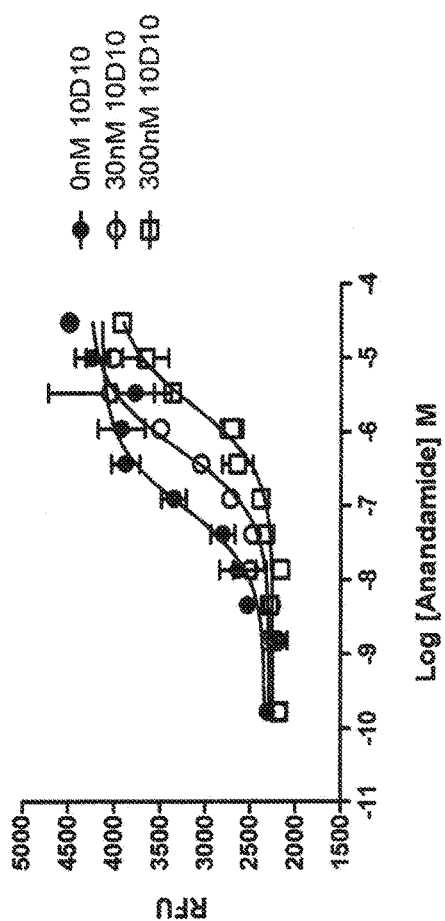
FIG. 6B shows concentration effects on GTP-Eu for differing concentrations of 10D10.

FIG. 6A shows that CB1 antibodies 10D10, 1E9 and 3H7 antagonize the endogenous CB1 agonist anandamide in a GTP-Eu assay. The small molecule antagonist SR 141716A was used as a comparator in this assay, and the $IC_{50}$ values for all four antagonists are shown in Table 6. FIG. 6B shows that increasing concentrations of 10D10 right-shift the dose response curve of anandamide in the GTP-Eu assay, further demonstrating the antagonist activity of 10D10.

TABLE 6

|  | $IC_{50}$ |
| --- | --- |
| 1E9 | $1.965 \times 10^{-8}$ M |
| 10D10 | $1.014 \times 10^{-8}$ M |
| 3H7 | $4.434 \times 10^{-8}$ M |
| SR 141716A | $8.915 \times 10^{-9}$ M |

Example 3

Several 10D10 mutants were prepared. Examples of tested antibodies were Y54143 has 10D10-Y54143 LC (SEQ ID No. 36) paired with 10D10-LYYY5.002 HC (SEQ ID No. 37), which contains a T144L mutation in the HC. Also Y54143-B has 10D10-Y54143 LC (SEQ ID No. 36) paired with 10D10-31Y.002 HC (SEQ ID No. 38). Sequences are shown below:

```
10D10-3141 LC
                                    (SEQ ID NO: 31)
DIVMTQSPLSLPVTPGEPASISCRSSQSLYHSYGYNYLDWYLQKPGQSPQ

LLIYLGYKKASGVPDRFSGSGSGTDFTLKISRVEAEDVGVYYCMQALQTP

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-3143 LC
                                    (SEQ ID NO: 32)
DIVMTQSPLSLPVTPGEPASISCRSSQSLYHSYGYNYLDWYLQKPGQSPQ

LLIYLGSNRASGVPDRFSGSGSGTDFTLKISRVEAEDVGVYYCMQARGTV

RTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

10D10-314143 LC
                                    (SEQ ID NO: 33)
DIVMTQSPLSLPVTPGEPASISCRSSQSLYHSYGYNYLDWYLQKPGQSPQ

LLIYLGYKKASGVPDRFSGSGSGTDFTLKISRVEAEDVGVYYCMQARGTV

RTFGQGTKVEIKRTVAAPSVFIFPPSDEQLKSGTASVVCLLNNFYPREAK
```

-continued

VQWKVDNALQSGNSQESVTEQDSKDSTYSLSSTLTLSKADYEKHKVYACE
VTHQGLSSPVTKSFNRGEC

10D10-Y541 LC
(SEQ ID NO: 34)
DIVMTQSPLSLPVTPGEPASISCRSSQSLLHYYGYNYLDWYLQKPGQSPQ
LLIYLGYKKASGVPDRFSGSGSGTDFTLKISRVEAEDVGVYYCMQALQTP
RTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

10D10-Y543 LC
(SEQ ID NO: 35)
DIVMTQSPLSLPVTPGEPASISCRSSQSLLHYYGYNYLDWYLQKPGQSPQ
LLIYLGSNRASGVPDRFSGSGSGTDFTLKISRVEAEDVGVYYCMQARGTV
RTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

10D10-Y54143 LC
(SEQ ID NO: 36)
DIVMTQSPLSLPVTPGEPASISCRSSQSLLHYYGYNYLDWYLQKPGQSPQ
LLIYLGYKKASGVPDRFSGSGSGTDFTLKISRVEAEDVGVYYCMQARGTV
RTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

10D10-LYYY5.002 HC
(SEQ ID NO: 37)
QVQLQESGPGLVKPSQTLSLTCTVSGGSIRRGGDYWSWIRQHPGKGLEWI
GYIYYSGSTNYNPSLKSRATISVDTSKNQFSLKLSSVTAADTAVYYCARD
YDILTGYSYYYYGMDVWGQGTLVTVSSASTKGPSVFPLAPCSRSTSESTA
ALGCLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTT
PPMLDSDGSFFLYSKLTVDKSRWQQGNVFSCSVMHEALHNHYTQKSLSLS
PGK

10D10-31Y.002 HC
(SEQ ID NO: 38)
QVQLQESGPGLVKPSQTLSLTCTVSGGSIRRGGDYWSWIRQHPGKGLEWI
GYIYYSGSTLYNPRLKSRATISVDTSKNQFSLKLSSVTAADTAVYYCARD
YDILTGYSYYYYGMDVWGQGTLVTVSSASTKGPSVFPLAPCSRSTSESTA
ALGCLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTT

-continued

PPMLDSDGSFFLYSKLTVDKSRWQQGNVFSCSVMHEALHNHYTQKSLSLS
PGK

10D10 Mutant LC and HC with Proline Substitutions
10D10-Y54143-LP1 LC
(SEQ ID NO: 39)
DIVMTQSPLSLPVTPGEPASISCRSSQSLLHYYGYNYLDWYLQKPGQSPQ
LLIYLGYKKASGVPDRFSGSGSGTDFTLKISRVEAEDVGVYYCMQARGTV
PTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC 10D10-Y54143-LP2 LC
(SEQ ID NO: 40)
DIVMTQSPLSLPVTPGEPASISCRSSQSLLHYYGYNYLDWYLQKPGQSPQ
LLIYLGYKKASGVPDRFSGSGSGTDFTLKISRVEAEDVGVYYCMQPRGTV
RTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC 10D10-Y54143-LP3 LC
(SEQ ID NO: 41)
DIVMTQSPLSLPVTPGEPASISCRSSQSLLHYYGYNYLDWYLQKPGQSPQ
LLIYLGYKKASGVPDRFSGSGSGTDFTLKISRVEAEDVGVYYCMQPRGTV
PTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC 10D10-Y54143-HP1 HC
(SEQ ID NO: 42)
QVQLQESGPGLVKPSQTLSLTCTVSGGSIRRGGDYWSWIRQHPGKGLEWI
GYIYYSGSTLYNPRLKSRATISVDTSKNQFSLKLSSVTAADTAVYYCARD
YDPLTGYSYYYYGMDVWGQGTLVTVSSASTKGPSVFPLAPCSRSTSESTA
ALGCLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTT
PPMLDSDGSFFLYSKLTVDKSRWQQGNVFSCSVMHEALHNHYTQKSLSLS
PGK 10D10-Y54143-HP2 HC
(SEQ ID NO: 43)
QVQLQESGPGLVKPSQTLSLTCTVSGGSIRRGGDYWSWIRQHPGKGLEWI
GYIYYSGSTLYNPRLKSRATISVDTSKNQFSLKLSSVTAADTAVYYCARD
YDIPTGYSYYYYGMDVWGQGTLVTVSSASTKGPSVFPLAPCSRSTSESTA
ALGCLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTT -continued
```
PPMLDSDGSFFLYSKLTVDKSRWQQGNVFSCSVMHEALHNHYTQKSLSLS
PGK 10D10-Y54143-HP3 HC
                                          (SEQ ID NO: 44)
QVQLQESGPGLVKPSQTLSLTCTVSGGSIRRGGDYWSWIRQHPGKGLEWI

GYIYYSGSTLYNPRLKSRATISVDTSKNQFSLKLSSVTAADTAVYYCARD

YDILTGYSYYYYGMDPWGQGTLVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS
PGK

10D10-Y54143-HP4 HC
                                          (SEQ ID NO: 45)
QVQLQESGPGLVKPSQTLSLTCTVSGGSIRRGGDYWSWIRQHPGKGLEWI

GYIYYSGSTLYNPRLKSRATISVDTSKNQFSLKLSSVTAADTAVYYCARD

YDPPTGYSYYYYGMDVWGQGTLVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS
PGK

10D10-Y54143-HP5 HC
                                          (SEQ ID NO: 46)
QVQLQESGPGLVKPSQTLSLTCTVSGGSIRRGGDYWSWIRQHPGKGLEWI

GYIYYSGSTLYNPRLKSRATISVDTSKNQFSLKLSSVTAADTAVYYCARD

YDPLTGYSYYYYGMDPWGQGTLVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS
PGK

10D10-Y54143-HP6 HC
                                          (SEQ ID NO: 47)
QVQLQESGPGLVKPSQTLSLTCTVSGGSIRRGGDYWSWIRQHPGKGLEWI

GYIYYSGSTLYNPRLKSRATISVDTSKNQFSLKLSSVTAADTAVYYCARD

YDIPTGYSYYYYGMDPWGQGTLVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS
PGK

10D10-Y54143-HP7 HC
                                          (SEQ ID NO: 48)
QVQLQESGPGLVKPSQTLSLTCTVSGGSIRRGGDYWSWIRQHPGKGLEWI

GYIYYSGSTLYNPRLKSRATISVDTSKNQFSLKLSSVTAADTAVYYCARD

YDPPTGYSYYYYGMDPWGQGTLVTVSSASTKGPSVFPLAPCSRSTSESTA

ALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLS
PGK
```

Figure 7:
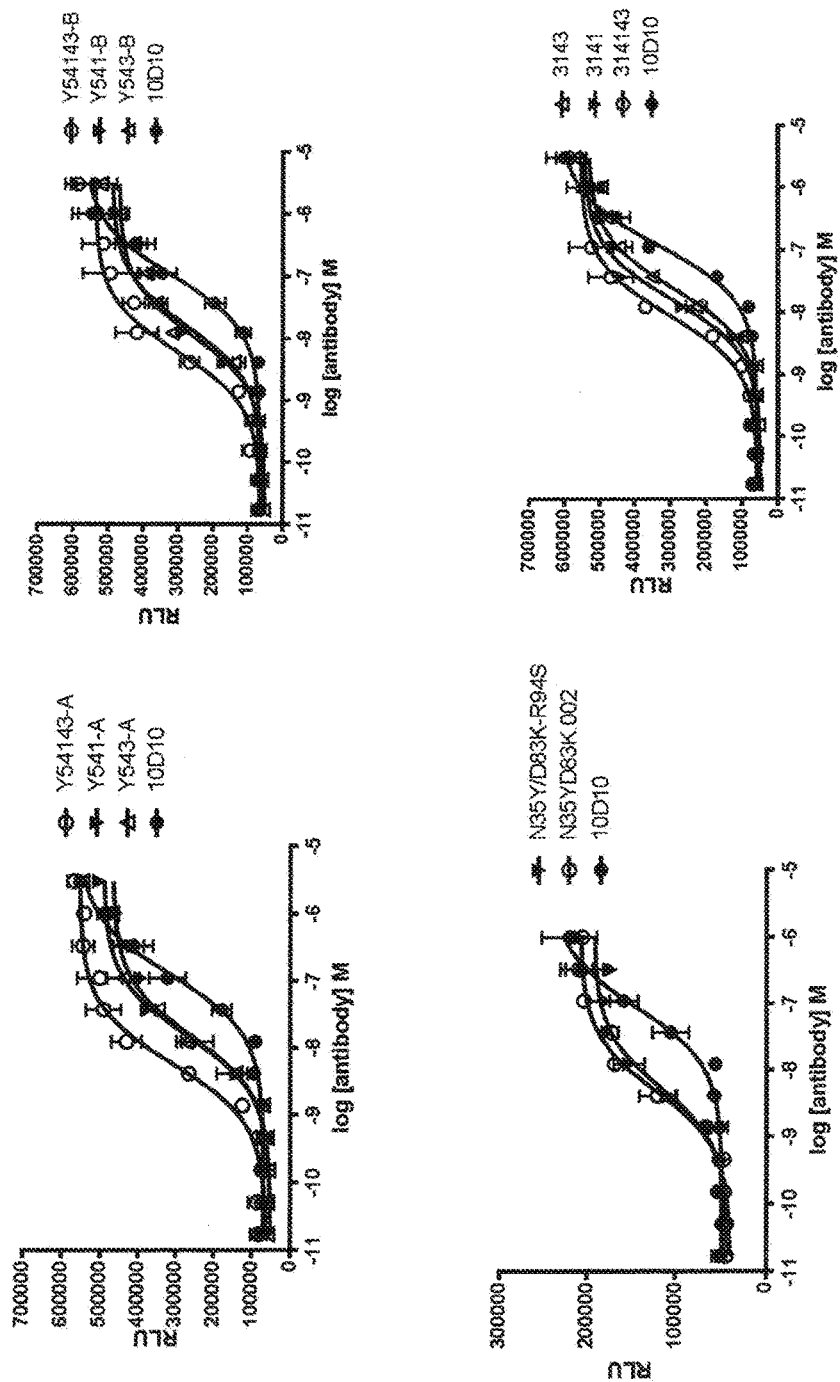
FIG. 7 presents activity of CB1 various mutans of CB1 antagonist antibodies.

FIG. 7 shows the results of several of these mutants. It can be seen that several mutant had increased potency relative to 10D10 as indicated by the leftward shift in the curves. It should also be noted that several 10D10 antigen-binding proteins with proline substitutions that were tested did not show increased potency relative to Y54143.

Throughout this specification various publications, patents and patent applications have been referenced. The disclosures of these documents in their entireties are hereby incorporated by reference into this application. The reference to such documents, however, should not be construed as an acknowledgment that such documents are prior art to the application. Further, merely because a document may be incorporated by reference, this does not necessarily indicate that the applicants are in complete agreement with the document's contents.

What is claimed:

1. A monoclonal antibody or antigen-binding fragment wherein the antibody or antigen-binding fragment thereof comprises a heavy chain variable region comprising complementarity determining regions (CDRs) designated H1, H2, and H3 and a light chain variable region comprising CDRs designated L1, L2, and L3, wherein H1, H2, and H3 have the sequence of SEQ ID NO: 17, 18, and 19, respectively, and L1, L2, and L3 have the sequence of SEQ ID NO: 20, 21, and 22, respectively.

2. A monoclonal antibody or antigen-binding fragment thereof of claim 1, wherein:
   (a) the heavy chain comprises the sequence of SEQ ID NO: 4 and the light chain comprises the sequence of SEQ ID NO: 5;
   (b) the heavy chain comprises the sequence of SEQ ID NO: 4 and the light chain comprises the sequence of SEQ ID NO: 14;
   (c) the heavy chain comprises the sequence of SEQ ID NO: 4 and the light chain comprises the sequence of SEQ ID NO: 8;
   (d) the heavy chain comprises the sequence of SEQ ID NO: 7 and the light chain comprises the sequence of SEQ ID NO: 8;
   (e) the heavy chain comprises the sequence of SEQ ID NO: 7 and the light chain comprises the sequence of SEQ ID NO: 10;
   (f) the heavy chain comprises the sequence of SEQ ID NO: 7 and the light chain comprises the sequence of SEQ ID NO: 12;
   (g) the heavy chain comprises the sequence of SEQ ID NO: 6 and the light chain comprises the sequence of SEQ ID NO: 16;
   (h) the heavy chain comprises the sequence of SEQ ID NO: 37 and the light chain comprises the sequence of SEQ ID NO: 36; or
   (i) the heavy chain comprises the sequence of SEQ ID NO: 38 and the light chain comprises the sequence of SEQ ID NO: 36.

3. The monoclonal antibody or antigen binding fragment thereof of claim 1 wherein the antibody or antigen-binding fragment thereof antagonizes G-protein signaling of the cannabinoid receptor-1 ("CB1") receptor.

4. The monoclonal antibody or antigen-binding fragment thereof of claim 1, wherein the antibody or antigen-binding fragment thereof has an EC50 between 69 nm-100 nM in a cAMP assay.

5. The monoclonal antibody or antigen-binding fragment thereof of claim 2, wherein the antibody or antigen-binding fragment thereof has an EC50 less than 100 nM in a cAMP assay.

6. The monoclonal antibody or antigen-binding fragment thereof of claim 1, wherein the antibody is a human antibody.

7. The monoclonal antibody or antigen-binding fragment thereof of claim 2, wherein the antibody is a human antibody.

8. A composition comprising the antibody or antigen-binding fragment thereof of claim 2 and a pharmaceutically acceptable carrier, diluent or excipient.

9. A nucleic acid encoding the antibody of claim 2.

10. An expression vector comprising the nucleic acid of claim 9.

11. An isolated host cell comprising the expression vector of claim 10.

12. A method of producing an antibody comprising culturing the host cell of claim 11 under suitable conditions such that antibody encoded by the expression vector is produced, and recovering the antibody from the host cell culture.

13. A method for inhibiting the activity of the human CB1 receptor in a subject in need thereof comprising administering to the subject an antibody or antigen-binding fragment thereof of claim 2.

14. The method of claim 13, wherein the subject has a metabolic disorder.

15. The method of claim 14, wherein the metabolic disorder is diabetes or obesity.

16. A method for improving a metabolic parameter in a subject in need thereof comprising administering to the subject an antibody or antigen-binding fragment thereof of claim wherein one or more metabolic parameters is improved in the subject following administration of the antibody or antigen-binding fragment thereof.

17. The method of claim 16, wherein the improved metabolic parameter is reduced plasma glucose, reduced insulin levels, reduced triglyceride levels, reduced HbA1c, reduced intraabdominal liver fat, reduced blood pressure, increased adiponectin, increased HDL, increased cholesterol or increased energy expenditure.

* * * * *

SEQUENCE LISTING

```
<160> NUMBER OF SEQ ID NOS: 48

<210> SEQ ID NO 1
<211> LENGTH: 472
<212> TYPE: PRT
<213> ORGANISM: Homo sapiens

<400> SEQUENCE: 1
```

```
Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
            20                  25                  30

Ile Lys Gly Asp Met Ala Ser Lys Leu Gly Tyr Phe Pro Gln Lys Phe
        35                  40                  45

Pro Leu Thr Ser Phe Arg Gly Ser Pro Phe Gln Glu Lys Met Thr Ala
    50                  55                  60

Gly Asp Asn Pro Gln Leu Val Pro Ala Asp Gln Val Asn Ile Thr Glu
65                  70                  75                  80

Phe Tyr Asn Lys Ser Leu Ser Ser Phe Lys Glu Asn Glu Glu Asn Ile
            85                  90                  95

Gln Cys Gly Glu Asn Phe Met Asp Ile Glu Cys Phe Met Val Leu Asn
                100                 105                 110

Pro Ser Gln Gln Leu Ala Ile Ala Val Leu Ser Leu Thr Leu Gly Thr
            115                 120                 125

Phe Thr Val Leu Glu Asn Leu Leu Val Leu Cys Val Ile Leu His Ser
    130                 135                 140

Arg Ser Leu Arg Cys Arg Pro Ser Tyr His Phe Ile Gly Ser Leu Ala
145                 150                 155                 160

Val Ala Asp Leu Leu Gly Ser Val Ile Phe Val Tyr Ser Phe Ile Asp
                165                 170                 175

Phe His Val Phe His Arg Lys Asp Ser Arg Asn Val Phe Leu Phe Lys
            180                 185                 190

Leu Gly Gly Val Thr Ala Ser Phe Thr Ala Ser Val Gly Ser Leu Phe
        195                 200                 205

Leu Thr Ala Ile Asp Arg Tyr Ile Ser Ile His Arg Pro Leu Ala Tyr
    210                 215                 220

Lys Arg Ile Val Thr Arg Pro Lys Ala Val Val Ala Phe Cys Leu Met
225                 230                 235                 240

Trp Thr Ile Ala Ile Val Ile Ala Val Leu Pro Leu Leu Gly Trp Asn
                245                 250                 255

Cys Glu Lys Leu Gln Ser Val Cys Ser Asp Ile Phe Pro His Ile Asp
            260                 265                 270

Glu Thr Tyr Leu Met Phe Trp Ile Gly Val Thr Ser Val Leu Leu Leu
        275                 280                 285

Phe Ile Val Tyr Ala Tyr Met Tyr Ile Leu Trp Lys Ala His Ser His
    290                 295                 300

Ala Val Arg Met Ile Gln Arg Gly Thr Gln Lys Ser Ile Ile Ile His
305                 310                 315                 320

Thr Ser Glu Asp Gly Lys Val Gln Val Thr Arg Pro Asp Gln Ala Arg
                325                 330                 335

Met Asp Ile Arg Leu Ala Lys Thr Leu Val Leu Ile Leu Val Val Leu
            340                 345                 350

Ile Ile Cys Trp Gly Pro Leu Leu Ala Ile Met Val Tyr Asp Val Phe
        355                 360                 365

Gly Lys Met Asn Lys Leu Ile Lys Thr Val Phe Ala Phe Cys Ser Met
    370                 375                 380

Leu Cys Leu Leu Asn Ser Thr Val Asn Pro Ile Ile Tyr Ala Leu Arg
385                 390                 395                 400

Ser Lys Asp Leu Arg His Ala Phe Arg Ser Met Phe Pro Ser Cys Glu
                405                 410                 415
```

Gly Thr Ala Gln Pro Leu Asp Asn Ser Met Gly Asp Ser Asp Cys Leu
            420                 425                 430

His Lys His Ala Asn Asn Ala Ala Ser Val His Arg Ala Ala Glu Ser
        435                 440                 445

Cys Ile Lys Ser Thr Val Lys Ile Ala Lys Val Thr Met Ser Val Ser
    450                 455                 460

Thr Asp Thr Ser Ala Glu Ala Leu
465             470

<210> SEQ ID NO 2
<211> LENGTH: 473
<212> TYPE: PRT
<213> ORGANISM: Mus sp.

<400> SEQUENCE: 2

Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
            20                  25                  30

Ile Lys Gly Asp Met Ala Ser Lys Leu Gly Tyr Phe Pro Gln Lys Phe
        35                  40                  45

Pro Leu Thr Ser Phe Arg Gly Ser Pro Phe Gln Glu Lys Met Thr Ala
    50                  55                  60

Gly Asp Asn Ser Pro Leu Val Pro Ala Gly Asp Thr Thr Asn Ile Thr
65                  70                  75                  80

Glu Phe Tyr Asn Lys Ser Leu Ser Ser Phe Lys Glu Asn Glu Asp Asn
                85                  90                  95

Ile Gln Cys Gly Glu Asn Phe Met Asp Met Glu Cys Phe Met Ile Leu
            100                 105                 110

Asn Pro Ser Gln Gln Leu Ala Ile Ala Val Leu Ser Leu Thr Leu Gly
        115                 120                 125

Thr Phe Thr Val Leu Glu Asn Leu Leu Val Leu Cys Val Ile Leu His
    130                 135                 140

Ser Arg Ser Leu Arg Cys Arg Pro Ser Tyr His Phe Ile Gly Ser Leu
145                 150                 155                 160

Ala Val Ala Asp Leu Leu Gly Ser Val Ile Phe Val Tyr Ser Phe Val
                165                 170                 175

Asp Phe His Val Phe His Arg Lys Asp Ser Pro Asn Val Phe Leu Phe
            180                 185                 190

Lys Leu Gly Gly Val Thr Ala Ser Phe Thr Ala Ser Val Gly Ser Leu
        195                 200                 205

Phe Leu Thr Ala Ile Asp Arg Tyr Ile Ser Ile His Arg Pro Leu Ala
    210                 215                 220

Tyr Lys Arg Ile Val Thr Arg Pro Lys Ala Val Val Ala Phe Cys Leu
225                 230                 235                 240

Met Trp Thr Ile Ala Ile Val Ile Ala Val Leu Pro Leu Leu Gly Trp
                245                 250                 255

Asn Cys Lys Lys Leu Gln Ser Val Cys Ser Asp Ile Phe Pro Leu Ile
            260                 265                 270

Asp Glu Thr Tyr Leu Met Phe Trp Ile Gly Val Thr Ser Val Leu Leu
        275                 280                 285

Leu Phe Ile Val Tyr Ala Tyr Met Tyr Ile Leu Trp Lys Ala His Ser
    290                 295                 300

His Ala Val Arg Met Ile Gln Arg Gly Thr Gln Lys Ser Ile Ile Ile
305                 310                 315                 320

His Thr Ser Glu Asp Gly Lys Val Gln Val Thr Arg Pro Asp Gln Ala
                325                 330                 335

Arg Met Asp Ile Arg Leu Ala Lys Thr Leu Val Leu Ile Leu Val Val
            340                 345                 350

Leu Ile Ile Cys Trp Gly Pro Leu Leu Ala Ile Met Val Tyr Asp Val
        355                 360                 365

Phe Gly Lys Met Asn Lys Leu Ile Lys Thr Val Phe Ala Phe Cys Ser
    370                 375                 380

Met Leu Cys Leu Leu Asn Ser Thr Val Asn Pro Ile Ile Tyr Ala Leu
385                 390                 395                 400

Arg Ser Lys Asp Leu Arg His Ala Phe Arg Ser Met Phe Pro Ser Cys
                405                 410                 415

Glu Gly Thr Ala Gln Pro Leu Asp Asn Ser Met Gly Asp Ser Asp Cys
            420                 425                 430

Leu His Lys His Ala Asn Asn Thr Ala Ser Met His Arg Ala Ala Glu
        435                 440                 445

Ser Cys Ile Lys Ser Thr Val Lys Ile Ala Lys Val Thr Met Ser Val
    450                 455                 460

Ser Thr Asp Thr Ser Ala Glu Ala Leu
465                 470

<210> SEQ ID NO 3
<211> LENGTH: 473
<212> TYPE: PRT
<213> ORGANISM: Rattus sp.

<400> SEQUENCE: 3

Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
            20                  25                  30

Ile Lys Gly Asp Met Ala Ser Lys Leu Gly Tyr Phe Pro Gln Lys Phe
        35                  40                  45

Pro Leu Thr Ser Phe Arg Gly Ser Pro Phe Gln Glu Lys Met Thr Ala
    50                  55                  60

Gly Asp Asn Ser Pro Leu Val Pro Ala Gly Asp Thr Thr Asn Ile Thr
65                  70                  75                  80

Glu Phe Tyr Asn Lys Ser Leu Ser Ser Phe Lys Glu Asn Glu Glu Asn
                85                  90                  95

Ile Gln Cys Gly Glu Asn Phe Met Asp Met Glu Cys Phe Met Ile Leu
            100                 105                 110

Asn Pro Ser Gln Gln Leu Ala Ile Ala Val Leu Ser Leu Thr Leu Gly
        115                 120                 125

Thr Phe Thr Val Leu Glu Asn Leu Leu Val Leu Cys Val Ile Leu His
    130                 135                 140

Ser Arg Ser Leu Arg Cys Arg Pro Ser Tyr His Phe Ile Gly Ser Leu
145                 150                 155                 160

Ala Val Ala Asp Leu Leu Gly Ser Val Ile Phe Val Tyr Ser Phe Val
                165                 170                 175

Asp Phe His Val Phe His Arg Lys Asp Ser Pro Asn Val Phe Leu Phe
            180                 185                 190

Lys Leu Gly Gly Val Thr Ala Ser Phe Thr Ala Ser Val Gly Ser Leu
        195                 200                 205

Phe Leu Thr Ala Ile Asp Arg Tyr Ile Ser Ile His Arg Pro Leu Ala

```
            210                 215                 220

Tyr Lys Arg Ile Val Thr Arg Pro Lys Ala Val Val Ala Phe Cys Leu
225                 230                 235                 240

Met Trp Thr Ile Ala Ile Val Ile Ala Val Leu Pro Leu Leu Gly Trp
                    245                 250                 255

Asn Cys Lys Lys Leu Gln Ser Val Cys Ser Asp Ile Phe Pro Leu Ile
                260                 265                 270

Asp Glu Thr Tyr Leu Met Phe Trp Ile Gly Val Thr Ser Val Leu Leu
            275                 280                 285

Leu Phe Ile Val Tyr Ala Tyr Met Tyr Ile Leu Trp Lys Ala His Ser
        290                 295                 300

His Ala Val Arg Met Ile Gln Arg Gly Thr Gln Lys Ser Ile Ile Ile
305                 310                 315                 320

His Thr Ser Glu Asp Gly Lys Val Gln Val Thr Arg Pro Asp Gln Ala
                325                 330                 335

Arg Met Asp Ile Arg Leu Ala Lys Thr Leu Val Leu Ile Leu Val Val
                340                 345                 350

Leu Ile Ile Cys Trp Gly Pro Leu Leu Ala Ile Met Val Tyr Asp Val
            355                 360                 365

Phe Gly Lys Met Asn Lys Leu Ile Lys Thr Val Phe Ala Phe Cys Ser
        370                 375                 380

Met Leu Cys Leu Leu Asn Ser Thr Val Asn Pro Ile Ile Tyr Ala Leu
385                 390                 395                 400

Arg Ser Lys Asp Leu Arg His Ala Phe Arg Ser Met Phe Pro Ser Cys
                405                 410                 415

Glu Gly Thr Ala Gln Pro Leu Asp Asn Ser Met Gly Asp Ser Asp Cys
                420                 425                 430

Leu His Lys His Ala Asn Asn Thr Ala Ser Met His Arg Ala Ala Glu
            435                 440                 445

Ser Cys Ile Lys Ser Thr Val Lys Ile Ala Lys Val Thr Met Ser Val
        450                 455                 460

Ser Thr Asp Thr Ser Ala Glu Ala Leu
465                 470

<210> SEQ ID NO 4
<211> LENGTH: 453
<212> TYPE: PRT
<213> ORGANISM: Homo sapiens

<400> SEQUENCE: 4

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
            100                 105                 110
```

```
Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 5
<211> LENGTH: 219
<212> TYPE: PRT
<213> ORGANISM: Homo sapiens

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 6
<211> LENGTH: 453
<212> TYPE: PRT
<213> ORGANISM: Homo sapiens

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Ala Thr Ile Ser Val Lys Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu

```
            180                 185                 190
Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 7
<211> LENGTH: 453
<212> TYPE: PRT
<213> ORGANISM: Homo sapiens

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Leu Tyr Asn Pro Arg
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg Asp Tyr Asp Ile Leu Thr Gly Tyr Ser Tyr Tyr Tyr
                100                 105                 110

Gly Met Asp Val Trp Gly Gln Gly Thr Thr Val Thr Val Ser Ser Ala
    115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 8
<211> LENGTH: 219
<212> TYPE: PRT
<213> ORGANISM: Homo sapiens

<400> SEQUENCE: 8

Asp Ile Val Met Thr Gln Ser Pro Leu Ser Leu Pro Val Thr Pro Gly
1               5                   10                  15
```

-continued

Glu Pro Ala Ser Ile Ser Cys Arg Ser Ser Gln Ser Leu Tyr His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 219
<212> TYPE: PRT
<213> ORGANISM: Homo sapiens

<400> SEQUENCE: 9

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Tyr His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser

```
                         165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 219
<212> TYPE: PRT
<213> ORGANISM: Homo sapiens

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 219
<212> TYPE: PRT
<213> ORGANISM: Homo sapiens

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 12
<211> LENGTH: 219
<212> TYPE: PRT
<213> ORGANISM: Homo sapiens

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

Arg Gly Thr Val Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 13
<211> LENGTH: 219
<212> TYPE: PRT
<213> ORGANISM: Homo sapiens

<400> SEQUENCE: 13

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Thr Val Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 219
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

-continued

```
Leu Gln Thr Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 15
<211> LENGTH: 219
<212> TYPE: PRT
<213> ORGANISM: Homo sapiens

<400> SEQUENCE: 15

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
                20                  25                  30

Tyr Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 16
<211> LENGTH: 219
<212> TYPE: PRT
<213> ORGANISM: Homo sapiens

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 17
<211> LENGTH: 7
<212> TYPE: PRT
<213> ORGANISM: Homo sapiens

<400> SEQUENCE: 17

Arg Gly Gly Asp Tyr Trp Ser
1               5

<210> SEQ ID NO 18
<211> LENGTH: 16
<212> TYPE: PRT
<213> ORGANISM: Homo sapiens

<400> SEQUENCE: 18

Tyr Ile Tyr Tyr Ser Gly Ser Thr Asn Tyr Asn Pro Ser Leu Lys Ser
1               5                   10                  15

<210> SEQ ID NO 19
<211> LENGTH: 17
<212> TYPE: PRT
<213> ORGANISM: Homo sapiens

<400> SEQUENCE: 19

Asp Tyr Asp Ile Leu Thr Gly Tyr Ser Tyr Tyr Tyr Tyr Gly Met Asp
1               5                   10                  15

Val

<210> SEQ ID NO 20
<211> LENGTH: 16
<212> TYPE: PRT
<213> ORGANISM: Homo sapiens

<400> SEQUENCE: 20

Arg Ser Ser Gln Ser Leu Leu His Ser Asn Gly Tyr Asn Tyr Leu Asp
1               5                   10                  15

<210> SEQ ID NO 21
<211> LENGTH: 7
<212> TYPE: PRT
<213> ORGANISM: Homo sapiens

<400> SEQUENCE: 21

Leu Gly Ser Asn Arg Ala Ser
1               5

<210> SEQ ID NO 22
<211> LENGTH: 9
<212> TYPE: PRT
<213> ORGANISM: Homo sapiens

<400> SEQUENCE: 22

Met Gln Ala Leu Gln Thr Pro Arg Thr
1               5

<210> SEQ ID NO 23
<211> LENGTH: 30
<212> TYPE: PRT
<213> ORGANISM: Homo sapiens

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg
            20                  25                  30

<210> SEQ ID NO 24
<211> LENGTH: 14
<212> TYPE: PRT
<213> ORGANISM: Homo sapiens

<400> SEQUENCE: 24

Trp Ile Arg Gln His Pro Gly Lys Gly Leu Glu Trp Ile Gly
1               5                   10

<210> SEQ ID NO 25
<211> LENGTH: 32
<212> TYPE: PRT
<213> ORGANISM: Homo sapiens

<400> SEQUENCE: 25

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 26
<211> LENGTH: 16
<212> TYPE: PRT
<213> ORGANISM: Homo sapiens

```
<400> SEQUENCE: 26

Tyr Ile Tyr Tyr Ser Gly Ser Thr Tyr Tyr Asn Pro Ser Leu Lys Ser
1               5                   10                  15

<210> SEQ ID NO 27
<211> LENGTH: 32
<212> TYPE: PRT
<213> ORGANISM: Homo sapiens

<400> SEQUENCE: 27

Arg Ala Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
                20                  25                  30

<210> SEQ ID NO 28
<211> LENGTH: 23
<212> TYPE: PRT
<213> ORGANISM: Homo sapiens

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys
                20

<210> SEQ ID NO 29
<211> LENGTH: 15
<212> TYPE: PRT
<213> ORGANISM: Homo sapiens

<400> SEQUENCE: 29

Trp Tyr Leu Gln Lys Pro Gly Gln Ser Pro Gln Leu Leu Ile Tyr
1               5                   10                  15

<210> SEQ ID NO 30
<211> LENGTH: 31
<212> TYPE: PRT
<213> ORGANISM: Homo sapiens

<400> SEQUENCE: 30

Gly Val Pro Asp Arg Phe Ser Gly Ser Gly Ser Gly Thr Asp Phe Thr
1               5                   10                  15

Leu Lys Ile Arg Arg Val Glu Ala Glu Asp Val Gly Tyr Tyr Cys
                20                  25                  30

<210> SEQ ID NO 31
<211> LENGTH: 219
<212> TYPE: PRT
<213> ORGANISM: Homo sapiens

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Tyr His Ser
                20                  25                  30

Tyr Gly Tyr Asn Tyr Leu Asp Trp Tyr Leu Gln Lys Pro Gly Gln Ser
            35                  40                  45

Pro Gln Leu Leu Ile Tyr Leu Gly Tyr Lys Ala Ser Gly Val Pro
        50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Met Gln Ala
                    85                  90                  95

Leu Gln Thr Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 32
<211> LENGTH: 219
<212> TYPE: PRT
<213> ORGANISM: Homo sapiens

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Tyr His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                    85                  90                  95

Arg Gly Thr Val Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 33
<211> LENGTH: 219
<212> TYPE: PRT
<213> ORGANISM: Homo sapiens

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Tyr His Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Thr Val Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 34
<211> LENGTH: 219
<212> TYPE: PRT
<213> ORGANISM: Homo sapiens

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110
```

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 218
<212> TYPE: PRT
<213> ORGANISM: Homo sapiens

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Thr Val Arg Thr Phe Gly Gln Gly Thr Lys Val Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu
    210                 215

<210> SEQ ID NO 36
<211> LENGTH: 219
<212> TYPE: PRT
<213> ORGANISM: Homo sapiens

<400> SEQUENCE: 36

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Thr Val Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 37
<211> LENGTH: 453
<212> TYPE: PRT
<213> ORGANISM: Homo sapiens

<400> SEQUENCE: 37

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
            100                 105                 110

Gly Met Asp Val Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160
```

```
Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 38
<211> LENGTH: 453
<212> TYPE: PRT
<213> ORGANISM: Homo sapiens

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Leu Tyr Asn Pro Arg
    50                  55                  60

Leu Lys Ser Arg Ala Thr Ile Ser Val Asp Thr Ser Lys Asn Gln Phe
```

```
              65                  70                  75                  80
        Ser Leu Lys Leu Ser Ser Val Thr Ala Ala Asp Thr Ala Val Tyr Tyr
                         85                  90                  95

Cys Ala Arg Asp Tyr Asp Ile Leu Thr Gly Tyr Ser Tyr Tyr Tyr Tyr
                        100                 105                 110

Gly Met Asp Val Trp Gly Gln Gly Thr Leu Val Thr Val Ser Ser Ala
                        115                 120                 125

Ser Thr Lys Gly Pro Ser Val Phe Pro Leu Ala Pro Cys Ser Arg Ser
                130                 135                 140

Thr Ser Glu Ser Thr Ala Ala Leu Gly Cys Leu Val Lys Asp Tyr Phe
        145                 150                 155                 160

Pro Glu Pro Val Thr Val Ser Trp Asn Ser Gly Ala Leu Thr Ser Gly
                        165                 170                 175

Val His Thr Phe Pro Ala Val Leu Gln Ser Ser Gly Leu Tyr Ser Leu
                        180                 185                 190

Ser Ser Val Val Thr Val Pro Ser Ser Asn Phe Gly Thr Gln Thr Tyr
                        195                 200                 205

Thr Cys Asn Val Asp His Lys Pro Ser Asn Thr Lys Val Asp Lys Thr
                210                 215                 220

Val Glu Arg Lys Cys Cys Val Glu Cys Pro Pro Cys Pro Ala Pro Pro
        225                 230                 235                 240

Val Ala Gly Pro Ser Val Phe Leu Phe Pro Pro Lys Pro Lys Asp Thr
                        245                 250                 255

Leu Met Ile Ser Arg Thr Pro Glu Val Thr Cys Val Val Val Asp Val
                        260                 265                 270

Ser His Glu Asp Pro Glu Val Gln Phe Asn Trp Tyr Val Asp Gly Val
                        275                 280                 285

Glu Val His Asn Ala Lys Thr Lys Pro Arg Glu Glu Gln Phe Asn Ser
                        290                 295                 300

Thr Phe Arg Val Val Ser Val Leu Thr Val Val His Gln Asp Trp Leu
        305                 310                 315                 320

Asn Gly Lys Glu Tyr Lys Cys Lys Val Ser Asn Lys Gly Leu Pro Ala
                        325                 330                 335

Pro Ile Glu Lys Thr Ile Ser Lys Thr Lys Gly Gln Pro Arg Glu Pro
                        340                 345                 350

Gln Val Tyr Thr Leu Pro Pro Ser Arg Glu Glu Met Thr Lys Asn Gln
                        355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
        385                 390                 395                 400

Pro Pro Met Leu Asp Ser Asp Gly Ser Phe Phe Leu Tyr Ser Lys Leu
                        405                 410                 415

Thr Val Asp Lys Ser Arg Trp Gln Gln Gly Asn Val Phe Ser Cys Ser
                        420                 425                 430

Val Met His Glu Ala Leu His Asn His Tyr Thr Gln Lys Ser Leu Ser
                        435                 440                 445

Leu Ser Pro Gly Lys
                450

<210> SEQ ID NO 39
<211> LENGTH: 219
<212> TYPE: PRT
<213> ORGANISM: Homo sapiens
```

<400> SEQUENCE: 39

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Thr Val Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 40
<211> LENGTH: 219
<212> TYPE: PRT
<213> ORGANISM: Homo sapiens

<400> SEQUENCE: 40

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95

Arg Gly Thr Val Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 41
<211> LENGTH: 219
<212> TYPE: PRT
<213> ORGANISM: Homo sapiens

<400> SEQUENCE: 41

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Tyr Lys Lys Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95

Arg Gly Thr Val Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 42
<211> LENGTH: 453
<212> TYPE: PRT
<213> ORGANISM: Homo sapiens

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

```
Gly Asp Tyr Trp Ser Trp Ile Arg Gln His Pro Gly Lys Gly Leu Glu
         35                  40                  45

Trp Ile Gly Tyr Ile Tyr Tyr Ser Gly Ser Thr Leu Tyr Asn Pro Arg
     50                  55                  60

Leu Lys Ser Arg Ala Thr Ile Ser Val Asp Thr Ser Lys Asn Gln Phe
 65              70                  75                      80

Ser Leu Lys Leu Ser Ser Val Thr Ala Ala Asp Thr Ala Val Tyr Tyr
                 85                  90                  95

Cys Ala Arg Asp Tyr Asp Pro Leu Thr Gly Tyr Ser Tyr Tyr Tyr Tyr
             100             105             110

Gly Met Asp Val Trp Gly Gln Gly Thr Leu Val Thr Val Ser Ser Ala
             115             120             125

Ser Thr Lys Gly Pro Ser Val Phe Pro Leu Ala Pro Cys Ser Arg Ser
         130             135             140

Thr Ser Glu Ser Thr Ala Ala Leu Gly Cys Leu Val Lys Asp Tyr Phe
145             150             155             160

Pro Glu Pro Val Thr Val Ser Trp Asn Ser Gly Ala Leu Thr Ser Gly
             165             170             175

Val His Thr Phe Pro Ala Val Leu Gln Ser Ser Gly Leu Tyr Ser Leu
             180             185             190

Ser Ser Val Val Thr Val Pro Ser Ser Asn Phe Gly Thr Gln Thr Tyr
             195             200             205

Thr Cys Asn Val Asp His Lys Pro Ser Asn Thr Lys Val Asp Lys Thr
210             215             220

Val Glu Arg Lys Cys Cys Val Glu Cys Pro Pro Cys Pro Ala Pro Pro
225             230             235             240

Val Ala Gly Pro Ser Val Phe Leu Phe Pro Pro Lys Pro Lys Asp Thr
             245             250             255

Leu Met Ile Ser Arg Thr Pro Glu Val Thr Cys Val Val Val Asp Val
             260             265             270

Ser His Glu Asp Pro Glu Val Gln Phe Asn Trp Tyr Val Asp Gly Val
     275             280             285

Glu Val His Asn Ala Lys Thr Lys Pro Arg Glu Glu Gln Phe Asn Ser
     290             295             300

Thr Phe Arg Val Val Ser Val Leu Thr Val Val His Gln Asp Trp Leu
305             310             315             320

Asn Gly Lys Glu Tyr Lys Cys Lys Val Ser Asn Lys Gly Leu Pro Ala
             325             330             335

Pro Ile Glu Lys Thr Ile Ser Lys Thr Lys Gly Gln Pro Arg Glu Pro
             340             345             350

Gln Val Tyr Thr Leu Pro Pro Ser Arg Glu Glu Met Thr Lys Asn Gln
         355             360             365

Val Ser Leu Thr Cys Leu Val Lys Gly Phe Tyr Pro Ser Asp Ile Ala
370             375             380

Val Glu Trp Glu Ser Asn Gly Gln Pro Glu Asn Asn Tyr Lys Thr Thr
385             390             395             400

Pro Pro Met Leu Asp Ser Asp Gly Ser Phe Phe Leu Tyr Ser Lys Leu
             405             410             415

Thr Val Asp Lys Ser Arg Trp Gln Gln Gly Asn Val Phe Ser Cys Ser
             420             425             430

Val Met His Glu Ala Leu His Asn His Tyr Thr Gln Lys Ser Leu Ser
             435             440             445
```

```
Leu Ser Pro Gly Lys
    450

<210> SEQ ID NO 43
<211> LENGTH: 453
<212> TYPE: PRT
<213> ORGANISM: Homo sapiens

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Leu Tyr Asn Pro Arg
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Pro Thr Gly Tyr Ser Tyr Tyr Tyr Tyr
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

```
Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 44
<211> LENGTH: 453
<212> TYPE: PRT
<213> ORGANISM: Homo sapiens

<400> SEQUENCE: 44

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Arg Arg Gly
            20                  25                  30

Gly Asp Tyr Trp Ser Trp Ile Arg Gln His Pro Gly Lys Gly Leu Glu
            35                  40                  45

Trp Ile Gly Tyr Ile Tyr Tyr Ser Gly Ser Thr Leu Tyr Asn Pro Arg
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
            100                 105                 110

Gly Met Asp Pro Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
            195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
```

```
            275                 280                 285
Glu Val His Asn Ala Lys Thr Lys Pro Arg Glu Gln Phe Asn Ser
    290                 295                 300
Thr Phe Arg Val Val Ser Val Leu Thr Val Val His Gln Asp Trp Leu
305                 310                 315                 320
Asn Gly Lys Glu Tyr Lys Cys Lys Val Ser Asn Lys Gly Leu Pro Ala
                325                 330                 335
Pro Ile Glu Lys Thr Ile Ser Lys Thr Lys Gly Gln Pro Arg Glu Pro
            340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
            370                 375                 380
Val Glu Trp Glu Ser Asn Gly Gln Pro Glu Asn Asn Tyr Lys Thr Thr
385                 390                 395                 400
Pro Pro Met Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys
    450

<210> SEQ ID NO 45
<211> LENGTH: 453
<212> TYPE: PRT
<213> ORGANISM: Homo sapiens

<400> SEQUENCE: 45

Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Arg Arg Gly
            20                  25                  30
Gly Asp Tyr Trp Ser Trp Ile Arg Gln His Pro Gly Lys Gly Leu Glu
        35                  40                  45
Trp Ile Gly Tyr Ile Tyr Tyr Ser Gly Ser Thr Leu Tyr Asn Pro Arg
    50                  55                  60
Leu Lys Ser Arg Ala Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Tyr Asp Pro Pro Thr Gly Tyr Ser Tyr Tyr Tyr Tyr
                100                 105                 110
Gly Met Asp Val Trp Gly Gln Gly Thr Leu Val Thr Val Ser Ser Ala
            115                 120                 125
Ser Thr Lys Gly Pro Ser Val Phe Pro Leu Ala Pro Cys Ser Arg Ser
        130                 135                 140
Thr Ser Glu Ser Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
```

```
Ser Ser Val Val Thr Val Pro Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 46
<211> LENGTH: 453
<212> TYPE: PRT
<213> ORGANISM: Homo sapiens

<400> SEQUENCE: 46

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Leu Tyr Asn Pro Arg
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Pro Leu Thr Gly Tyr Ser Tyr Tyr Tyr Tyr
            100                 105                 110
```

Gly Met Asp Pro Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
            130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
            195                 200                 205

Thr Cys Asn Val Asp His Lys Pro Ser Asn Thr Lys Val Asp Lys Thr
            210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 47
<211> LENGTH: 453
<212> TYPE: PRT
<213> ORGANISM: Homo sapiens

<400> SEQUENCE: 47

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly

-continued

```
                20                  25                  30
Gly Asp Tyr Trp Ser Trp Ile Arg Gln His Pro Gly Lys Gly Leu Glu
             35                  40                  45
Trp Ile Gly Tyr Ile Tyr Tyr Ser Gly Ser Thr Leu Tyr Asn Pro Arg
 50                  55                  60
Leu Lys Ser Arg Ala Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
             85                  90                  95
Cys Ala Arg Asp Tyr Asp Ile Pro Thr Gly Tyr Ser Tyr Tyr Tyr Tyr
            100                 105                 110
Gly Met Asp Pro Trp Gly Gln Gly Thr Leu Val Thr Val Ser Ser Ala
            115                 120                 125
Ser Thr Lys Gly Pro Ser Val Phe Pro Leu Ala Pro Cys Ser Arg Ser
            130                 135                 140
Thr Ser Glu Ser Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                    165                 170                 175
Val His Thr Phe Pro Ala Val Leu Gln Ser Ser Gly Leu Tyr Ser Leu
                    180                 185                 190
Ser Ser Val Val Thr Val Pro Ser Ser Asn Phe Gly Thr Gln Thr Tyr
                    195                 200                 205
Thr Cys Asn Val Asp His Lys Pro Ser Asn Thr Lys Val Asp Lys Thr
            210                 215                 220
Val Glu Arg Lys Cys Cys Val Glu Cys Pro Pro Cys Pro Ala Pro Pro
225                 230                 235                 240
Val Ala Gly Pro Ser Val Phe Leu Phe Pro Pro Lys Pro Lys Asp Thr
                    245                 250                 255
Leu Met Ile Ser Arg Thr Pro Glu Val Thr Cys Val Val Val Asp Val
                    260                 265                 270
Ser His Glu Asp Pro Glu Val Gln Phe Asn Trp Tyr Val Asp Gly Val
            275                 280                 285
Glu Val His Asn Ala Lys Thr Lys Pro Arg Glu Glu Gln Phe Asn Ser
            290                 295                 300
Thr Phe Arg Val Val Ser Val Leu Thr Val Val His Gln Asp Trp Leu
305                 310                 315                 320
Asn Gly Lys Glu Tyr Lys Cys Lys Val Ser Asn Lys Gly Leu Pro Ala
                    325                 330                 335
Pro Ile Glu Lys Thr Ile Ser Lys Thr Lys Gly Gln Pro Arg Glu Pro
                    340                 345                 350
Gln Val Tyr Thr Leu Pro Pro Ser Arg Glu Glu Met Thr Lys Asn Gln
                    355                 360                 365
Val Ser Leu Thr Cys Leu Val Lys Gly Phe Tyr Pro Ser Asp Ile Ala
            370                 375                 380
Val Glu Trp Glu Ser Asn Gly Gln Pro Glu Asn Asn Tyr Lys Thr Thr
385                 390                 395                 400
Pro Pro Met Leu Asp Ser Asp Gly Ser Phe Phe Leu Tyr Ser Lys Leu
                    405                 410                 415
Thr Val Asp Lys Ser Arg Trp Gln Gln Gly Asn Val Phe Ser Cys Ser
                    420                 425                 430
Val Met His Glu Ala Leu His Asn His Tyr Thr Gln Lys Ser Leu Ser
            435                 440                 445
```

Leu Ser Pro Gly Lys
    450

<210> SEQ ID NO 48
<211> LENGTH: 453
<212> TYPE: PRT
<213> ORGANISM: Homo sapiens

<400> SEQUENCE: 48

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Leu Tyr Asn Pro Arg
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Pro Thr Gly Tyr Ser Tyr Tyr Tyr Tyr
            100                 105                 110

Gly Met Asp Pro Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln

```
                355                 360                 365
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```